US012350108B2

(12) United States Patent
Chatterjee et al.

(10) Patent No.: US 12,350,108 B2
(45) Date of Patent: Jul. 8, 2025

(54) WEARABLE IMAGING SYSTEM FOR MEASURING BONE DISPLACEMENT

(71) Applicant: Kinisi Inc, Santa Cruz, CA (US)

(72) Inventors: Manjirnath Agrahayan Chatterjee, Alameda, CA (US); Faisal Mohammed Mirza, Aptos, CA (US); Rajveen Rosie Sendher, Santa Cruz, CA (US)

(73) Assignee: Kinisi Inc., Santa Cruz, CA (US)

( * ) Notice: Subject to any disclaimer, the term of this patent is extended or adjusted under 35 U.S.C. 154(b) by 108 days.

(21) Appl. No.: 17/841,489

(22) Filed: Jun. 15, 2022

(65) Prior Publication Data

US 2022/0401079 A1 Dec. 22, 2022

Related U.S. Application Data

(60) Provisional application No. 63/211,378, filed on Jun. 16, 2021.

(51) Int. Cl.
*A61B 8/00* (2006.01)
*A61B 8/08* (2006.01)
*G16H 50/20* (2018.01)

(52) U.S. Cl.
CPC .......... *A61B 8/5223* (2013.01); *A61B 8/0875* (2013.01); *A61B 8/4477* (2013.01);
(Continued)

(58) Field of Classification Search
CPC ... A61B 8/5223; A61B 8/0875; A61B 8/4227; G16H 50/20; G06T 2207/10132; G06T 2207/20081; G06T 2207/20084
See application file for complete search history.

(56) References Cited

U.S. PATENT DOCUMENTS

2008/0194952 A1* 8/2008 Luo ............... A61B 8/0875
600/437
2012/0029345 A1* 2/2012 Mahfouz ............ A61B 5/0004
600/595

(Continued)

FOREIGN PATENT DOCUMENTS

DE 102017123388 A1 * 4/2019
WO WO 2020/101569 A1 5/2020

OTHER PUBLICATIONS

Mohabir, "Knee cartilage segmentation of ultrasound images using convolutional neural networks and local phase enhancement", 2020, Rutgers, The State University of New Jersey (Year: 2020).*

(Continued)

*Primary Examiner* — Colin T. Sakamoto
*Assistant Examiner* — Andrew W Begeman
(74) *Attorney, Agent, or Firm* — Fenwick & West LLP

(57) ABSTRACT

An embodiment of wearable imaging system implements a set of sensors distributed around the joint of a user with advanced software machine learning techniques to deliver accurate measurements of bone-to-bone displacement and angle. A first subset of the distributed sensors emit ultrasound signals towards the joint of the user and a second subset detects ultrasound signals traveling through and reflected off structures of the joint. A controller of the wearable imaging system extracts physiological properties of the joint from the detected ultrasound signals. The controller inputs the physiological properties of the joint and properties of the detected ultrasound signals to a machine-learned displacement model to generate a bone displacement measurement at the joint.

21 Claims, 14 Drawing Sheets

(52) U.S. Cl.
CPC ... *G16H 50/20* (2018.01); *G06T 2207/10132* (2013.01); *G06T 2207/20081* (2013.01); *G06T 2207/20084* (2013.01)

(56) References Cited

U.S. PATENT DOCUMENTS

| | | | |
|---|---|---|---|
| 2016/0038119 A1* | 2/2016 | Desjardins | A61B 8/4444 600/424 |
| 2017/0100092 A1* | 4/2017 | Kruse | G01S 15/8997 |

OTHER PUBLICATIONS

DE102017123388A1 (Valeo Schalter & Sensoren GMBH). Translated by Espacenet. Oct. 9, 2017 [retrieved May 2, 2024] (Year: 2017).*

PCT International Search Report and Written Opinion, PCT Application No. PCT/US22/33675, Sep. 12, 2022, 9 pages.

* cited by examiner

*Distributed Set of Sensors Integrated into a Knee Wrap*
225

*Integrated Sensor Array of a Fabric 250*

WEARABLE IMAGING SYSTEM FOR MEASURING BONE DISPLACEMENT

CROSS REFERENCE TO RELATED APPLICATIONS

This application claims the benefit of U.S. Provisional Patent Application No. 63/211,378, filed on Jun. 16, 2021, which is incorporated herein in its entirety for all purposes.

TECHNICAL FIELD

This disclosure relates generally to a wearable ultrasound imaging system and, more specifically, a form fitting dynamic sleeve integrated with a distributed set of sensors for measuring bone displacement and angle.

BACKGROUND

Conventional ultrasound imaging systems utilize reflected ultrasound waves to create imaging of the interior of the patient's body. Such techniques allow medical providers to visualize structures in the body by sending ultrasound pulses into the body via an ultrasound transducer and measuring the time for various reflections of the ultrasound pulses to be returned to the transducer. In implementations involving a distributed set of transducers, the arrival time of the reflected pulses may be slightly offset depending on the location of each transducer of the distributed set of sensors. Additionally, the reflection of transducer pulses may be used to determine the distance of the transducer from a particular element within the body (e.g., bone). By combining these distance measurements with the time delay of reflected transducer signals, an ultrasound system may determine the displacement of an interior element based on both the element itself and its relative distance from a transducer (e.g., based on the known measures of speed of sound in various body structures).

Conventional ultrasound systems include a handheld transducer attached by a cord to an ultrasound machine that powers a display on the machine itself. These systems apply ultrasound waves transmitted by the manually held transducer to the body of a patient and convert the ultrasound waves into image displayed on a screen. Such systems either require little to no motion from the patient or may tolerate limbs being repositioned to identify certain anatomic feature. They are highly dependent on the operator of the device and are based purely on optical interpretation of the images by the operator and/or radiologists that view the image. For example, a fetal ultrasound imaging system converts ultrasound waves into images based on the known density of human tissue. Measurements are taken manually and visually by an operator using software that overlays analytic tools on the images obtained. The patient being imaged cannot move while the operator applies the transducer to the outer surface of the patient's body. As another example, an ultrasound transducer may be applied to the neck region of patient to identify the location and characteristics of the carotid artery flow.

Additionally, existing ultrasound systems cannot measure the distance between two bones in a joint because they are unable to focus the reflected ultrasound wave in the spacing of the joint. For example, the patellofemoral joint shifts with knee flexion. The articulation of the patella with the distal femur changes as the knee moves from an extended to a flexed position or vice versa. The patella can tilt to either a medial or lateral side and translate from its typical position in the patellar groove of the distal femur. An ultrasound performed on the patellofemoral joint while the knee is extended may provide different information from when the knee is flexed or continuously moving. Further, the aforementioned movement of the patella may not be detected on a static ultrasound of the knee.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

I. Overview

A wearable imaging system measures displacement between two bones at a joint using a combination of distributed ultrasonic sensors and machine-learned models and techniques to generate real-time joint displacement estimate. The distributed sensors may be embedded into wearable sleeve. As a user moves while wearing the sleeve, the sensors emit ultrasound pulses while reflect off the bones of the joint. The wearable imaging system measures displacement in the bones of the joint based on the reflection patterns of the pulses, the arrangement and orientation of the distributed sensors within the sleeve, and correlations between reflections patterns over all sensors.

II. System Configuration

Figure 1:
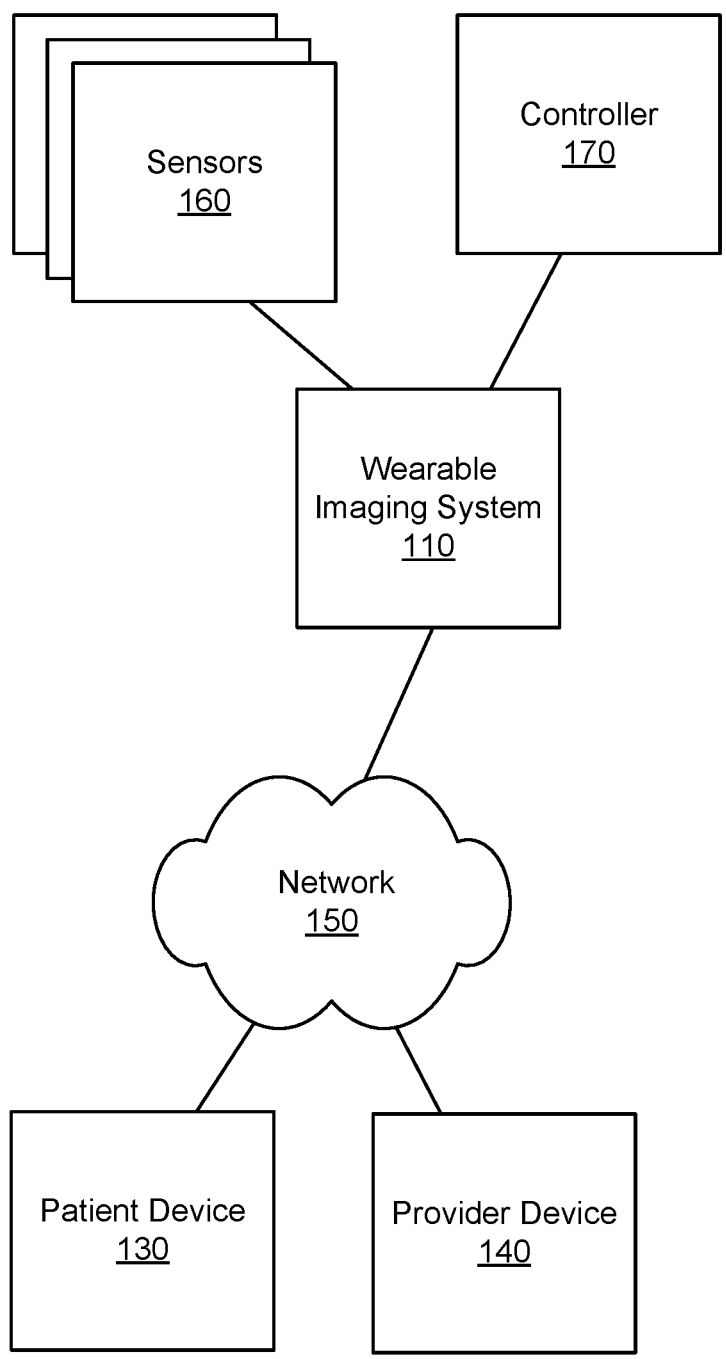
(FIG. 1 illustrates a system architecture for a digital brace system, according to one example embodiment.

FIG. (FIG. 1 illustrates an example system architecture for a portable ultrasound system 100. The portable ultrasound system 100 may include a wearable imaging system 110, a patient device 130, a provider device 140, and a network 150. The wearable imaging system includes one or more distributed sensors 160 and a controller 170 embedded into the wearable imaging system 110. Although FIG. 1 illustrates only a single instance of most of components of the wearable imaging system 100, in practice more than one of each component may be present, and additional or fewer components may be used.

The wearable imaging system 110 may include a plyowrap or any other apparatus capable of being worn by a patient over a joint (e.g., knee, ankle, elbow, wrist, shoulder) while moving. As described herein, a plyowrap is a dynamic sleeve designed with a pliable material that is capable of adapting to the dynamic movement of a joint without inhibiting the movement of the joint. The plyowrap may include a first end and a second end. Each end may include an opening through which an appendage may fit through. By fitting the appendage through the openings, the plyowrap may be fit (or worn) over a joint.

The plyowrap may be worn while the patient participates in activities including, but not limited to, any type of daily movement. During such activity, the plyowrap may be worn by a user around any joint to monitor, maintain, or improve the performance and function of the joint, which allows a clinician to assess bone to bone motion during these normal activities. For example, the plyowrap may measure aspects of joint motion, limb motion, spinal motion, or a combination thereof. The plyowrap may be structured in a variety of ways, for example, as a rectangular structure that wraps around a knee or a sleeve that is pulled up to the knee from the foot. Alternative embodiments of the plyowrap are additionally described herein. In some embodiments, the plyowrap may be configured with a support structure or frame to provide additional support to the joint or surrounding body parts. The frame may be coupled internally or externally the plyowrap. In such embodiments, the plyowrap of the wearable imaging system 10 may also be referred to as a "wearable brace."

In some embodiments, the plyowrap includes additional components and elements that allow the plyowrap to adjust its shape to accommodate the movement of the joint or to deliver a combination of nutrients to the patient to maintain or improve the performance of the joint. More information regarding such additional components and elements of the plyowrap can be found in U.S. patent application Ser. No. 17/351,157, which is incorporated by reference herein in its entirety. The wearable imaging system 110 described herein may be used in parallel with pertinent treatments to evaluate joint function and performance over a long period of time.

Sensors 160 are embedded within the plyowrap of the wearable imaging system 110 to collect data describing various aspects of the motion of the joint and to characterize the movement of the joint based on kinematic information, gait information, balance information regarding joint and body alignment, and/or kinematic function and activity determined from the collected sensor data. The sensors 160 may be integrated into the wearable imaging system 110 by weaving them into the plyowrap of the imaging system or another suitable material integration technique. In alternate embodiments, the sensors 160 are attached to the plyowrap using an adhesive or any other suitable attachment technique. In embodiments where the plyowrap 110 is worn over the knee of a user, the sensors 160 additionally collect balance information of the tibio-femoral and tibio-fibular patellofemoral movements.

In some embodiments described below, the sensors 160 may be ultrasound transducers that emit ultrasound pulses, which reflect off bones at a particular joint covered by the plyowrap. In addition, the sensors 160 may capture comprehensive data that provides precise information on gross and subtle movements of the joint and parts of the body surrounding the joint to provide feedback for adjusting the sleeve in real-time or near real-time to correct movement of the joint, detect irregular movements of the joint, or further increase performance of the joint in manner that conventional braces are incapable of More information regarding such comprehensive sensor data can be found in U.S. patent application Ser. No. 17/351,157, which is incorporated by reference herein in its entirety.

As described herein, a plyowrap is a dynamic sleeve designed with a pliable material that adheres to the body of a user and adapts to the dynamic movement of a joint without inhibiting the movement of the joint. The plyowrap may be worn by a user around any joint to monitor, maintain, or improve the performance and function of the joint. For example, the plyowrap may measure aspects of joint motion, limb motion, spinal motion, or a combination thereof. In some example embodiments, the plyowrap identifies changes in the activity regarding a joint or neuromusculoskeletal function by generating a digital contour map of the joint and body status and monitoring movement and function at various points in time based on continuous electronic recordings. The wrap may be structured in a variety of ways, for example, as a rectangular structure that wraps around a knee or a sleeve that is pulled up to the knee from the foot. Alternative embodiments of the plyowrap are additionally described herein. The arrangement of sensors 160 are further described below with reference to FIG. 2A-C.

The controller 170 receives data regarding the ultrasound pulses (e.g., signals) emitted by each sensor 160, for example a time when the sensor emitted the ultrasound pulse, a time when the sensor received the reflected ultrasound pulse, time elapsed between when the sensor emitted the ultrasound pulse and when each remaining sensor received the reflected pulse, or a combination thereof. In some embodiments, the time when a sensor received a reflected ultrasound pulse may also be characterized as the time when the sensor detected that the ultrasound pulse reflected or refracted off a bone of the patient. As described herein, such reflected and refracted pulses are referred to as "echoes."

The controller 170 may further apply one or more machine-learned models to the time elapsed for each sensor to measure the displacement of bones at the joint covered by the plyowrap. As described herein, displacement refers to any movement of one bone relative to one or more other bones in any three-dimensional plane or axis of movement in a joint, for example movement of the femur, tibia, fibula, patella. The one or more machine-learned models may be trained to determine correlations between reflection patterns over the distributed sensors 160 and the bone-to-bone displacement at a joint. Reflection patterns describe the orientation and position of the sensors 160 within the plyowrap and the time elapsed between the transmission of an ultrasound signal and the receipt of its echo for each sensor 160. The machine-learned models applied by the controller 170 are further described below with reference to FIG. 3.

The design and functionality of the wearable brace 110, the sensors 160, and the controller 170 are further discussed below with reference to FIGS. 2-9.

For ease of discussion, embodiments of the portable ultrasound system 100, and more specifically the wearable imaging system 110, are described herein with reference to a knee wrap, but a person having ordinary skill in the art would appreciate that the described portable ultrasound system 100 may be used to monitor bone displacement, performance, function, or a combination thereof of any joint of the human body (e.g., elbows, ankles, foot, wrists, hand, phalanges, metacarpals, shoulders, hips, spine). In addition to wearable joint or body sleeves, the plyowrap 110 may also be a glove, exosuit, or mechanical brace for therapeutic use. Because embodiments of a wearable imaging system 100 may be designed using a plyowrap without a frame, the knee brace itself may also be characterized as a "plyowrap." Accordingly, the principles described herein in the context of a knee brace may be applied to embodiments of "wraps," "plyowraps," or "dynamic sleeves" worn by a user around the knee or in other contexts.

The patient device 130 is a computing device through which a user of the wearable imaging device 110 may interact with the portable ultrasound system 100. Similarly, the provider device 140 is a computing device through which a medical provider or third-party entity overseeing the user of the wearable imaging device 110 may interact with the portable ultrasound system 100. The patient device 130 and the provider device 140 may be computer systems. An example physical implementation of such a system is more completely described with FIG. 7. Each of the patient device 130 and the provider device 140 are configured to communicate with the controller 170, the wearable imaging system 110, or both via the network 150. For example, via a wireless application stored on the patient device 130, a user can communicate instructions for the controller 170 to adjust the shape of the plyowrap of the wearable imaging system 110 or to deliver particular nutrients to the user.

The patient device 130 may also store third-party health monitoring applications that monitor various related aspects of the health of a user. The wearable device 110 and the brace feedback system 120 may communicate with such third-party applications to gain further insight into a patient's health. For example, a third-party application stored on the patient device 130 may communicate with a heart rate monitor on the patient's chest. Accordingly, the digital brace system 100, and more specifically the brace feedback system 120 and the wearable brace 110, may synchronize with the third party application to determine when the patient is in discomfort or is experiencing a symptom and supplement the data collected by the sensors with those determinations.

Similarly, a provider, trainer, or supervisor of the user (e.g., a patient) may operate the provider device 140 to communicate instructions to the controller 170 based on feedback or data recorded by the sensors 160. Accordingly, the wearable brace 110 may be used as a diagnostic tool by healthcare providers who monitor data received from sensors embedded in the plyowrap. Examples of other users operating a provider device 140 include, but are not limited to, an employer, a technician, a caregiver, a trainer, a coach, a physical therapist, a doctor, or a health care worker. The communication between the patient device 130 and the provider device 140 and other components of the digital brace system 100 may be wireless, for example, via a short-range communication protocol such as Bluetooth, cellular, Wi-Fi, Ant, Zigbee, Ultra-wide-band (UWB), or any other suitable wireless connection or long-range communication protocol (e.g., satellite-based radio transmitters at various frequencies such as long-range backscatter system, VHF, UHF or K-band, S- or X- or other such signals that can be received in space)

The network 150 represents the various wired and wireless communication pathways between the wearable brace 110, the device feedback system 120, the patient device 130, and the provider device 140 via network 150. Network 150 uses standard Internet communications technologies and/or protocols. Thus, the network 150 can include links using technologies such as Ethernet, IEEE 602.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), a custom binary encoding etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above. The network 150 may enable components of the digital brace system 100 to communicate using wireless connections, for example Bluetooth, cellular, Wi-Fi, Ant, Zigbee, or any other suitable wireless connection or long-range communication protocol.

III. STRUCTURE OF THE WEARABLE IMAGING SYSTEM

Figure 2A:
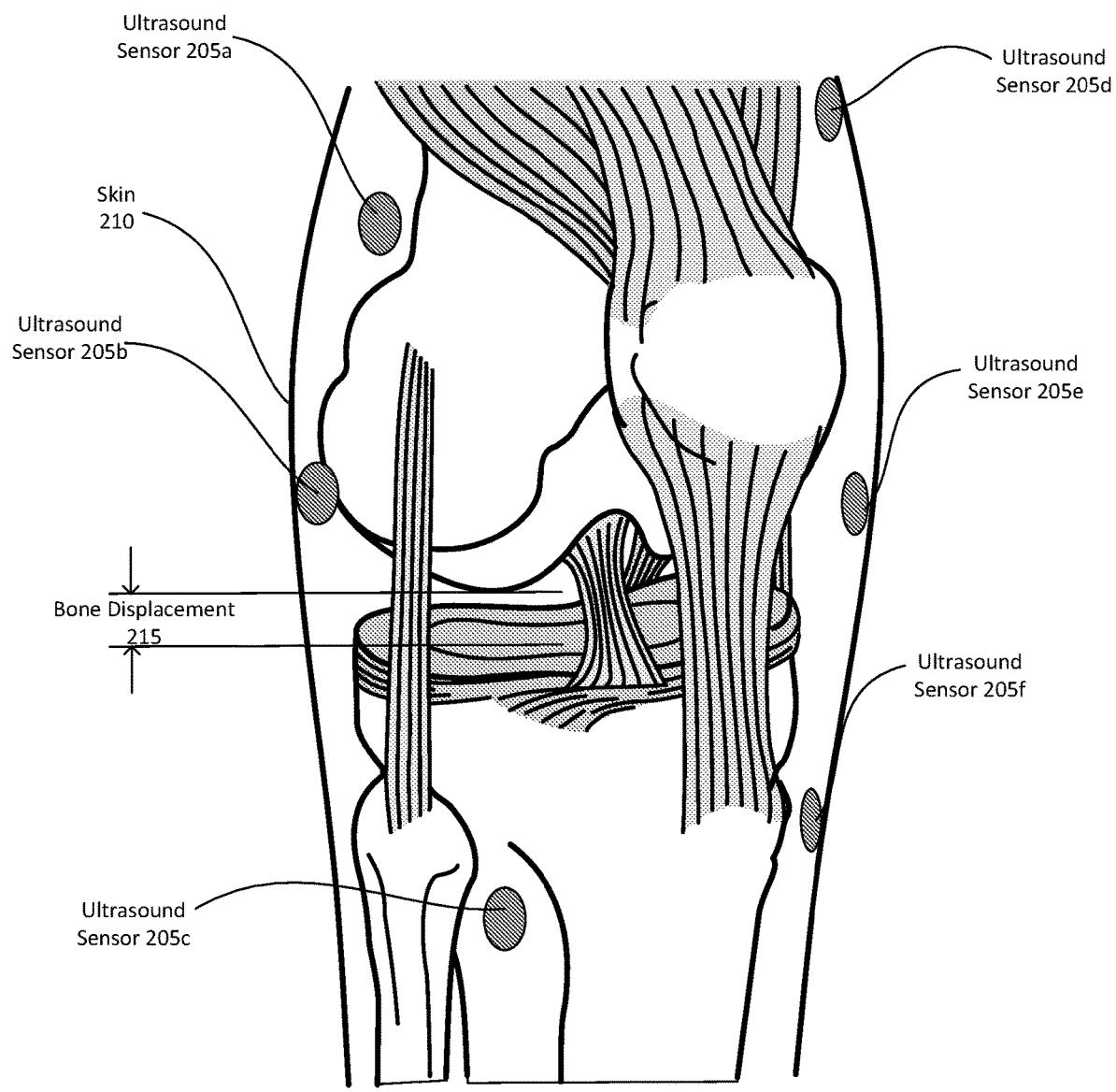
FIG. 2A is an illustration of a distributed set of ultrasound sensors placed directly on the skin around the knee, according to one example embodiment.

In one example embodiment of the wearable imaging device, the sensors 160 may be placed directly on skin of the user. FIG. 2A is an illustration of a distributed set of ultrasound sensors 205a-f (generally ultrasound sensor(s) 205) placed directly on the skin around the knee, according to one example embodiment. In the illustrated embodiment of FIG. 2A, the ultrasound sensors 205 are placed all along the skin 210 surrounding the joint and along the bones that meet at the knee. As will be discussed below, the wearable imaging system 110 processes ultrasound signals to characterize and/or measure the bone displacement 215.

In other embodiments, the distributed set of sensors may be integrated or embedded into "plyowrap" that the user secures around the joint of interest. As discussed above, the plyowrap may be worn over any joint of the body, for example the knee, the elbow, the wrist, or any other suitable joint. For illustrative purposes, the following description discusses embodiments in which the wearable imaging system includes a plyowrap used to cover the knee of a user, hereafter referred to as a "knee wrap." However, a person having ordinary skill in the art would appreciate that the description included herein may be applied to a plyowrap used to cover any other joint.

In some embodiments, the plyowrap is a tubular sleeve that may be pulled over the joint using anatomic features surrounding the joint to guide the placement and fit of the plyowrap. In such embodiments, the plyowrap may include graphic markers describing the anatomic orientation of the plyowrap. Alternatively, the plyowrap may be worn by folding the plyowrap over the joint using a securing mechanism to secure the plyowrap in place, for example a buckle, a clasp, a removable adhesive, or any other suitable securing mechanism.

In embodiments involving a knee wrap as discussed above, the placement and fit of the plyowrap of the knee wrap may be guided using some combination of the patella, tibial tubercle, the medial and lateral condyles, and any other suitable anatomic features of the knee. In embodiments of a knee wrap, for example the knee wrap illustrated in FIG. 2B, the wrap may include an opening or a socket to accommodate the position of the patella within the wrap. The knee wrap may further be designed to expose the back of the knee to improve the comfort of the user. The knee wrap may additionally be designed with vent holes in the area of the wrap covering the knee or any other body part around the knee to improve the breathability of the wrap.

The flexible, pliable material of the plyowrap conforms, when worn, to the shape of the joint of the user. Given the pliable nature of the material, the size and geometry of the plyowrap may vary depending on how the plyowrap is stretched based on size of the joint covered by the plyowrap and the movement of the joint covered by the plyowrap. In some embodiments, the circumference of the plyowrap is initially 5 centimeters before being stretched. Similarly, the cross-sectional thickness of the plyowrap may vary depending on the joint being covered, the size of the joint being covered, or the purpose for which the plyowrap is being used. In other embodiments, the plyowrap may be designed to accommodate a particular body type (e.g., toddlers, children, adults) or a particular user (e.g., a wrap customized for the user).

The flexible, pliable material of the plyowrap may be a natural or synthetic fabric or set of woven fabrics. As an example, the material may be a blend of materials including, but not limited to, neoprene, lycra, viscose, polyester, rubber, and natural fibers such as silk, cotton, hemp, or wool. The plyowrap may further be breathable, moisture wicking, moisture resistant, moisture repellant, or a combination thereof. In some embodiments, the knee wrap is electrically conductive. Alternatively, particular components of the knee wrap may be conductive.

In some embodiments, a support structure (e.g, a support frame) is integrated into the material of the plyowrap to provide additional support to the joint covered by the plyowrap. The support structure may be rigid and durable enough to prevent unexpected or damaging movements of the joint, but malleable enough to allow the plyowrap to conform to natural movements of the joint within the plyowrap. The support structure may have mechanical, hydraulic, electrochemical, electrical, and magnetic properties, or some combination thereof. In some embodiments, the support structure is a component covering some or all of the joint (e.g., a plastic, a metal, or any other suitable material). Alternatively, the support structure may be a semi-rigid strap wrapped around the joint. In some embodiments, the rigid properties of the support structure may be activated by an electrical signal indicating that the joint is moving beyond an acceptable or safe range of motion. More information regarding such electrical signals and components of the supports structure can be found in U.S. patent application Ser. No. 17/351,157, which is incorporated by reference herein in its entirety.

Figure 2B:
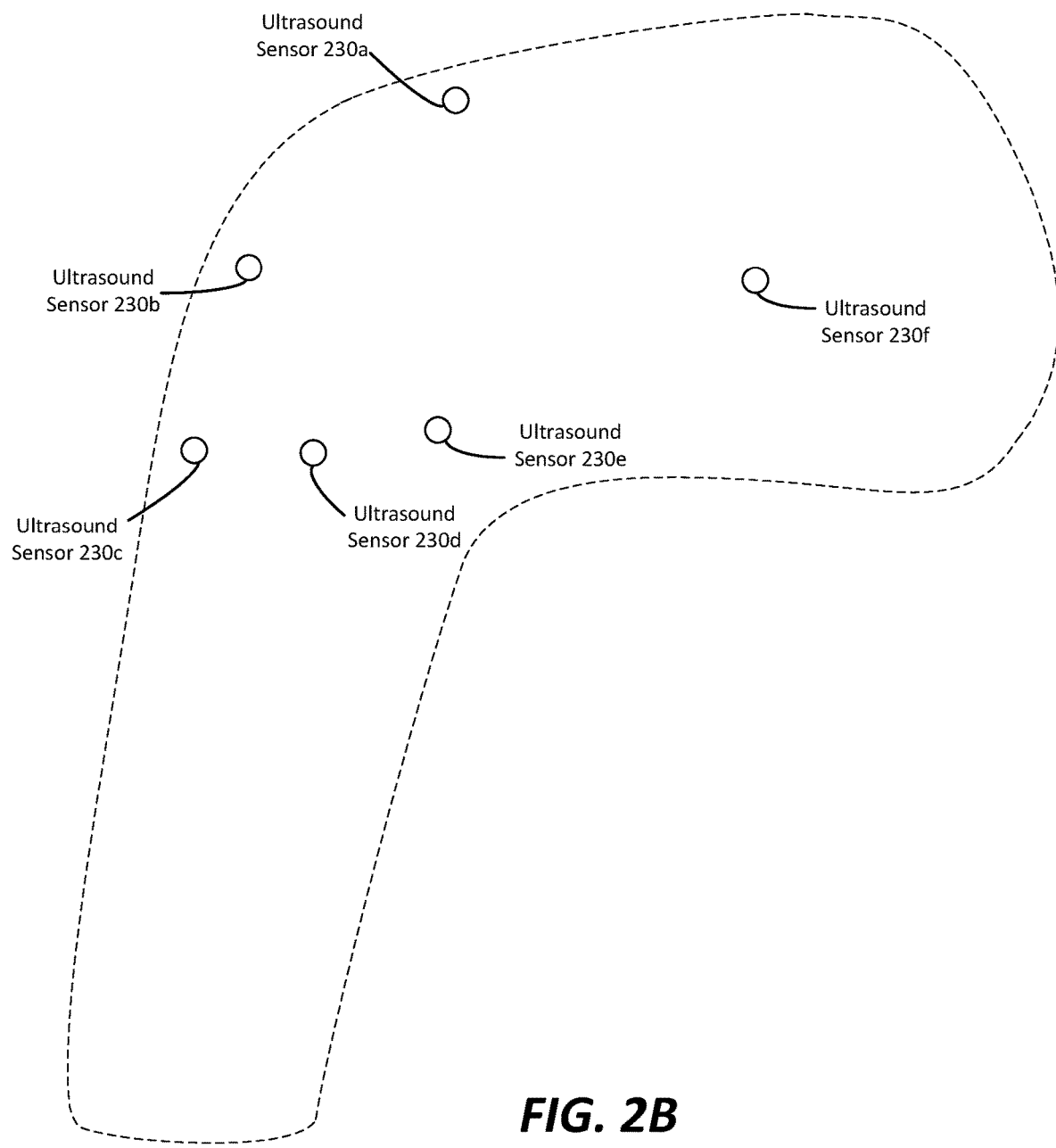
FIG. 2B is an illustration of a knee wrap that includes a distributed set of ultrasound sensors 230 that detect and characterize the relative position of bones around the knee, according to one example embodiment.

As discussed above, the plyowrap is integrated with a distributed set of sensors configured to measure and monitor bone-to-bone displacement of the joint while the user wears the plyowrap. FIG. 2B is an illustration of a knee wrap that includes a distributed set of ultrasound sensors that detect and characterize the relative position of bones around the knee, according to one example embodiment. In the illustrated embodiment, the knee wrap 225 includes one or more ultrasound sensors 230, which are placed around the knee (or any other joint corresponding to the plyowrap).

Each ultrasound sensor 230 of the distributed set emits an ultrasound signal including, but not limited to, a pulse or a spread function. For example, the ultrasound sensors 230 may be transducers that emit ultrasound signals in the form of pulses. In some embodiments, each ultrasound sensor 230 is connected to a gain controlled switchable amplifier. In a first implementation (referred to as a "sequential implementation"), each ultrasound sensor 230 of the distributed set is triggered separately. The triggered sensor 230 operates in transmission mode to transmit an ultrasound signal while the remaining sensors operate in detection mode to detect echoes of the transmitted ultrasound signal. As described herein, ultrasound sensors 230 operating in the transmission mode are referred to as "transmitters" and ultrasound sensors 230 operating in the detection mode are referred to as "detectors." This process of a single sensor 230 emitting a signal while the rest detect the signal is iterated sequentially across each sensor 230.

In a second implementation (also referred to as a "parallel implementation"), each ultrasound sensor 230 of the distribute set of sensors simultaneously operates in the transmission mode to emit an ultrasound signal while every other ultrasound sensor 230 operates in the detection mode. In the parallel implementation, the ultrasound signal emitted by each transmitter is encoded with a unique signature such that each detector may distinguish between signals emitted by different transmitters.

Both the sequential and parallel implementations of the sensors 160 are further discussed below with reference to FIGS. 3-5.

Although the distributed set of sensors 225 illustrated in FIG. 2B includes six ultrasound sensors 230a-f (generally, ultrasound sensor(s) 230), this embodiment is merely illustrative. In other embodiments, the distributed set of sensors 225 may include any number of sensors necessary to measure the displacements between the major bones of the knee (e.g., the tibia, femur, and patella) if the knee is subject to an unusual physiological condition, which results in an unusual echo or wavefront of an ultrasound signal. Examples of unusual physiological conditions include, but are not limited to, a calcified meniscus, an osteochondral fragment or fracture, an osteophyte, a ligament avulsion fracture, or recent kenalog (cortisone) injection containing calcium. An unusual echo or wavefront may additionally be caused where an individual suffered a prior fracture or injury that resulted in motion or anatomical variations of the joint outside of its typical anatomy, for example a pre-existing or genetic variation. Sensors of the distributed set 210 may be calibrated during the design of the knee wrap or at any point before a user begins using or wearing the knee wrap. For example, an unusual physiological condition may be validated by comparing the displacement predicted by the wearable imaging system 110 to a CTI or MTI scan of the joint.

In some embodiments, the ultrasound sensors 230 may infer fluidic flow through the knee correlated to blood flow, infer the flow of lubricating joint fluids when the joint is in motion due to movement, or a combination thereof In addition to the ultrasound sensors 230, the knee wrap may additionally be integrated with motion sensors (not shown) for measuring velocity, direction, location, or any other relevant characteristic of the movement of the knee. Examples of suitable motion sensors include, but are not limited to, accelerometers, gyroscopes, magnetometers, and physiological sensors for measuring heart rate and blood oxygen. The controller 170 may receive signals recorded by the motion sensors and extrapolate data regarding the movement of the joint (or a representation of the movement of the joint) and the physiological performance of the joint using machine-learned models, algorithms, or any other suitable computational tool. In some embodiments, the controller 220 compares data measured by the distributed set of sensors 210 for a particular user with a normalized dataset and patterns of motion to compare the performance of the user's joint with varying segments and demographics of populations or individuals. In some embodiments, the controller 170 correlates the received motion data with the ultrasound measurements determined based on signals received from the ultrasound sensors 230.

Although not shown, the knee wrap illustrated in FIG. 2B may also include the controller 170 and support electronics including, but not limited to, a battery (or alternate power source), and/or a communication circuit/chip (e.g., WiFi or Bluetooth). The communication circuit may be integrated with or communicatively coupled with the controller 220. The controller 170 and the support electronics may be embedded into the knee wrap (or plyowrap) and electronically coupled to the ultrasound sensors 230 and any motion sensors of the knee wrap. The controller 170 may be embedded into the knee wrap or integrated in a removable manner. In some embodiments (not shown) the controller 170 is contained in a housing structure, which may be embedded or removably integrated into the knee wrap to improve the durability of the controller 170 and prevent any damage to the controller caused by any element internal or external to the wearable brace. In alternate embodiments, the controller 170 may be communicatively coupled to the ultrasound sensors 230, such that processing by the controller 170 is performed remotely.

The controller 170 is a type of processing unit. The controller 170 receives signals from the ultrasound sensors 230 describing properties representative of the tissue surrounding the joint and the bones of the joint, for example the time delay between the transmitter's emission of an ultrasound signal and a particular detector's receipt of the signal, known physiological properties of the bones at the joint, known physiological properties of the tissue, or a combination thereof. Properties of the both the bones and the tissue surrounding the joint may be estimated based on the distributed ultrasound signals emitted and detected by the distributed set of sensors 225. Accordingly, the controller 220 may be any suitable circuit board, integrated circuit chip or communication panel configured to process and transmit signals encoded with measurements recorded by the ultrasound sensors 230. As will be discussed in further detail below, the controller 170 may input measurements extracted from the ultrasound signals transmitted by a sensor 230 and the reflected signals detected by the sensors 230 to a machine-learned model trained to generate prediction or measurement of bone displacement at the joint.

A battery is additionally embedded into the knee wrap to power other electrical components of the wrap, for example the distributed set of sensors 225, the controller 170, and individual sensors 230. The battery may be a rechargeable battery or a disposable battery. The battery may be fixed within the knee wrap and have a recharging port. Alternately, the battery may be removable from the knee wrap such that a user or provider may replace the battery and connect the electrical components to a new battery. In some embodiments, the battery itself and/or the connections between other electrical components and the battery are waterproof.

Figure 2C:
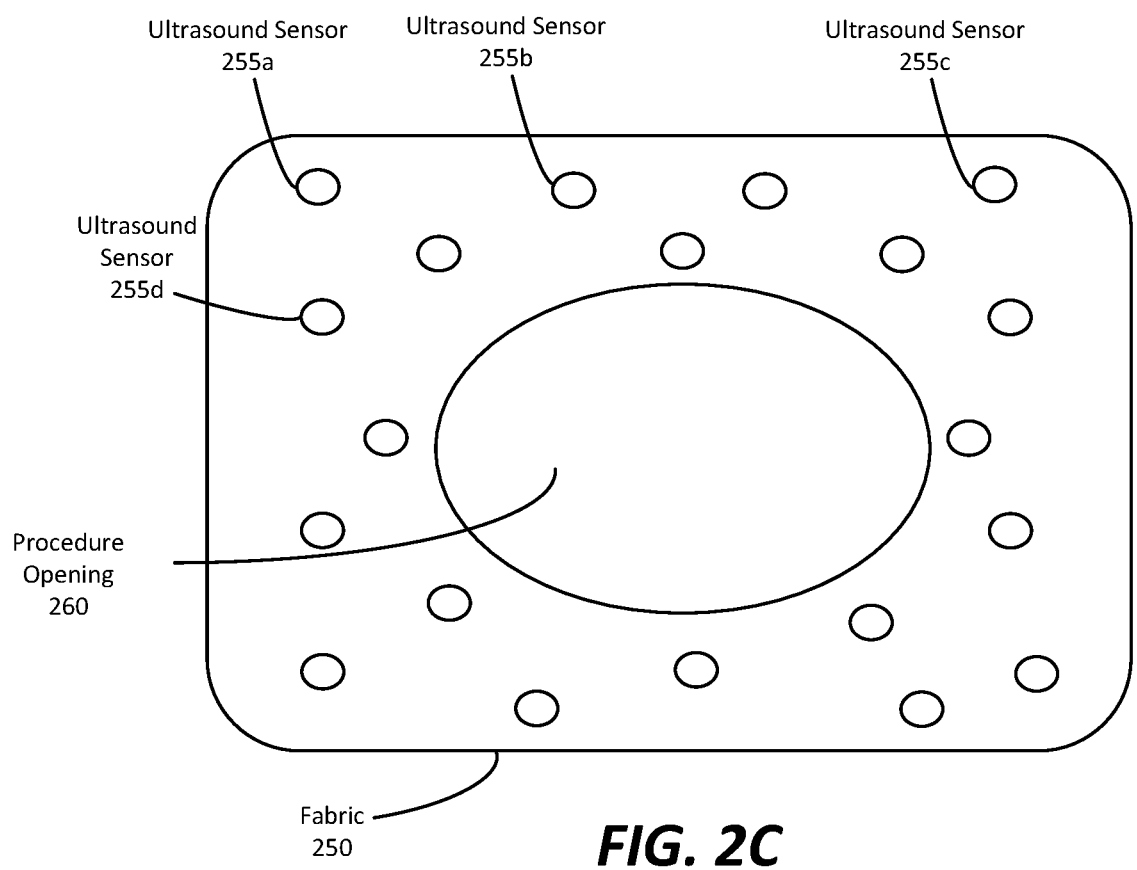
FIG. 2C is an illustration of a fabric 250 with an integrated, distributed set of ultrasound sensors 255 that detect and characterize the relative position of bones covered by the fabric, according to one example embodiment.

In another embodiment of the portable ultrasound system 100, a distributed set of ultrasound sensors is integrated into a fabric draped over a body part of a patient during surgery or an operation. Whereas in conventional systems the surgeon holds a transducer in one hand while operating with the other, the integration of the ultrasound sensors into the fabric allows the surgeon the freedom to use both hands. FIG. 2C is an illustration of a fabric 250 with an integrated array of ultrasound sensors 255 that detect and characterize the relative position of bones covered by the fabric, according to one example embodiment. The fabric 250 may be any shape or configuration necessary to conform to the geometry of the joint (e.g., a knee). Additionally, the fabric 250 may be further integrated with adhesives or any other suitable mechanism for securing the fabric 250 the skin of the user.

In the illustrated embodiment, the fabric 250 is integrated with a distributed set of ultrasound sensors 255 (e.g., sensors 255a, 255b, 255c, 255d; generally ultrasound sensor(s) 255). The ultrasound sensors 255 are functionally and technically consistent with the ultrasound sensors 205 and 235 discussed above with reference to FIGS. 2A and 2B. Additionally, the ultrasound sensors 255 may be integrated into the fabric 250 in the same manner that the ultrasound sensors 235 are integrated into the knee wrap. The ultrasound sensors 255 may be include gel pads, which may be sterilized depending on placement of the fabric 250 relative to sterilized portions of the patient's body.

The fabric further includes a procedure opening 260 located in the center of the fabric 250. The procedure opening 260 exposes the part of the body being operated on by the surgeon or another qualified medical practitioner. The procedure opening may be any size necessary to effectively carry out a surgery, intervention, or procedure or accommodate the requisite surgical instrument (e.g., needle, scalpel, trocar, screw, balloon, catheter, line, stent, implantable/partially implantable/non-implantable device) used during the procedure.

IV. Measuring Bone Displacement at a Joint

Figure 3:
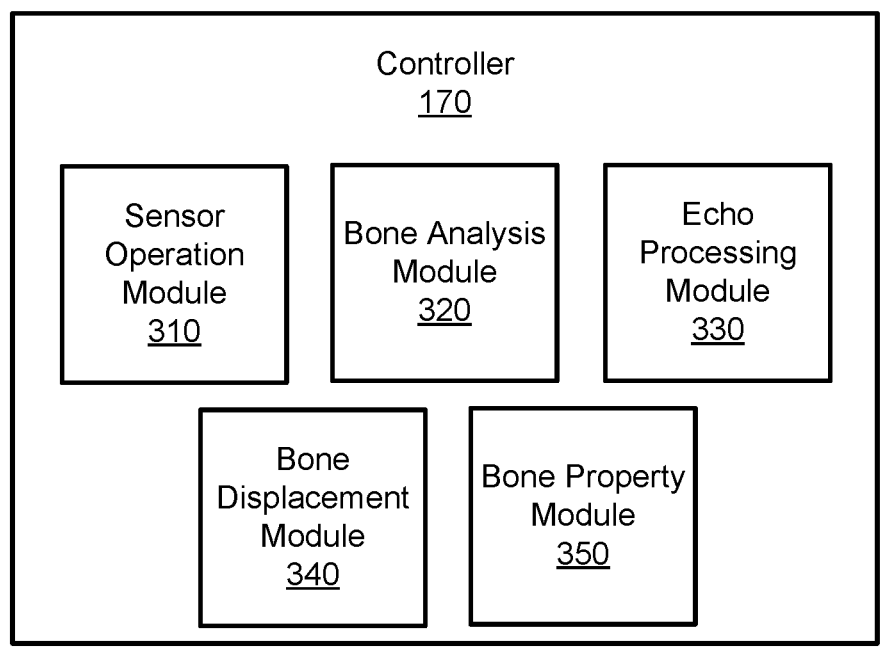
FIG. 3 is a block diagram of the system architecture of the controller 170 of the wearable ultrasound system 110, according to an example embodiment

FIG. 3 is a block diagram of the system architecture of the controller 170 of the wearable ultrasound system 110, according to an example embodiment. The controller 170 comprises a sensor operation module 310, a bone analysis module 320, an echo processing module 330, a bone displacement module 340, and a bone property module 350.

However, in other embodiments, the controller 170 may include different and/or additional components.

In the sequential implementation (also referred to as a "serial drive mode"), the sensor operation module 310 instructs a single ultrasound sensor to "drive" by emitting an ultrasound signal (e.g., an ultrasound pulse) amplified by the connected gain amplifier. As described herein, the ultrasound signal emitted by the transmitter is referred as the "drive signal." The sensor operation module 310 instructs all remaining ultrasound sensors to detect echoes created when the drive signal reflects off a bone at a joint. The transmitter emits the drive signal as formed shape, for example a biophase pulse. The detectors each receive the pulse representing the drive signal at different times and with varying time delays, which are a function of the distance between the detector and the transmitter, the reflection and refraction of ultrasound signals due to bone structures at the joint (e.g., bone-to-bone reflection resonances), or a combination thereof. Given the varying time delays, the sensor operation module 310 may instruct each detector to remain in the detection mode long enough to capture any and all reflections of the ultrasound signal. The time period which the detector remains in detection mod may also be referred to as the "active detection period." In some embodiments, the bone analysis module 320 determines the active detection period for maintaining the detectors in the detection mode based on the slowest possible sound wave propagation and the maximum possible distance between the two farthest sensors of the distributed set 200. For example, the bone analysis module 320 may determine the active detection period based on maximum distance between sensors of 500 mm and a sound wave propagation speed of 1400/m/s (e.g., the sound wave propagation speed measured for fatty tissue). In some embodiments, the bone analysis module 320 may dynamically adjust the active detection period based on a combination of factors including, but not limited to, changes in the position and orientation of ultrasound sensors 230, the performance of individual ultrasound sensors 230, and the physical properties of the tissue surrounding the joint (e.g., softness or hardness of the tissue).

In a second implementation (also referred to as a "parallel implementation"), each ultrasound sensor 230 of the distributed set of sensors simultaneously operates in the transmission mode to emit an ultrasound signal while every other ultrasound sensor 230 operates in the detection mode. That is, the sensor operation module 310 switches each ultrasound sensor into transmission mode and each transmitter emits a drive signal. In some embodiments, each transmitter emits a drive signal encoded orthogonal to the other transmitters. Transmission of orthogonally encoded signals (e.g., a frequency multiplexed signal, a code-division multiplexed signal, or symbol multiplexed signal) enables the simultaneous transmission of multiple unique signals that may be recovered without inter-symbol interference. Accordingly, orthogonally encoded signals are effectively implemented in high density shared-medium communication systems.

As discussed above, sensor operation module 310 encodes the drive signal emitted by each transmitter with a unique signature identifying its transmitter. After every transmitter of the distributed set of sensors emits a drive signal, the sensor operation module 310 transitions every emitter into the detection mode. Accordingly, each detector receives a complex signal (either a direct drive signal or an indirect echo of a drive signal) that is the superposition of each sensor's unique orthogonal encoding and a function of the bone displacement. The sensor operation module 310 applies signal processing techniques to encode each detector to identify the transmitter responsible for emitting the directly detected drive signal or the echo of a drive signal.

A person having ordinary skill in the art would appreciate that the techniques described herein for processing signals received by detectors into predictions regarding bone displacement at a joint may be applied in either a sequential implementation or a parallel implementation.

When a transmitter emits a drive signal, the detectors may receive multiple copies of the pulse, for example a first direct pulse representing the shortest path and other echoes representing longer paths involving reflections and refractions of the drive signal. In embodiments where a transmitter and a detector are positioned on the same side of the joint (or body part), the detector may receive a drive signal with a direct path through the soft tissue around the joint. In embodiments where the transmitter and the detector are positioned on opposite sides of the join (or body part), the detector may receive a drive signal with a direct path through multiple layers of soft tissues and/or bone. After receiving the first drive signal, each detector may additionally receive echoes of the original drive signal caused by reflections or refractions of the drive signal off the bone. For example, where a detector and a transducer are located on the same side of a joint or body part, the detector will first detect a drive signal that travels directly through soft tissue surrounding the joint, followed by echoes bouncing off the bone.

After each detector of the distributed set of sensors has either directly detected the drive signal or detected an echo of the drive signal, the sensor operation module 310 transitions the transmitter into the detection mode and selects a detector to transition into transmission mode. The sensor operation module 310 maintains the unselected detectors in detection mode. The new transmitter transmits a new drive signal which is received either directly or as an echo by the new detector and the existing detectors. This process is repeated until each sensor of the distributed set has emitted a drive signal as a transmitter and the drive signal is received by each detector. The controller 170 may perform the processing techniques described below continuously as the sensor operation module 310 transitions and operates sensors of the distributed set of sensors or at once after all signals have been emitted and received.

The echo processing module 830 distinguishes between signals detected by the detector that were transmitted directly from the transmitter and those that were reflected or refracted off of bone structures before being directed to the detector. When an echo is received at a detector, the echo processing module 830 may synchronize the timing of the echo with the shape of its waveform relative to the waveforms of echoes receives at other detectors. Accordingly, the echo processing module 830 triangulates which parts of the joint anatomy caused the reflections/refractions of the echo based on any combination of the shape, size, or time received of the waveform. In a sequential implementation, the echo processing module 830 may determine a time domain reconstruction of varying echoes and determine which edges (e.g., boundary conditions in the physiology) generated the particular wavefronts using multi-path algorithms. In a parallel implementation, the echo processing module 830 may determine which portions of an echo came from which transmitter is done by demodulating the signal's encoding. Depending on the location of some physiological features of the joint, some echoes may be stronger than others even when deeper in the tissue. The echo processing module 830 may determine the distance between those physiological features based on the timing of the received waveform signals and improves resolution of the detected physiological features by combining the determined distance with other echoes received at a various locations. The echo processing module 330 analyzes the signals received to determine the distance between the transmitter and each detector of the distributed set of sensors.

In some embodiments, the bone displacement module 340 implements a first machine learned model—a sensor distance model—to receive, as inputs, direct drive signals and echoes of a drive signal received by each detector of a distributed set of sensors and to generate, as an output, a predicted distance between the detector and a transmitter that emitted the drive signal. Accordingly, the echo processing module may apply machine-learning techniques to model (or predict) distances between ultrasound sensors integrated into a plyowrap.

The echo processing module 330 may further comprise a signal digitizer (not shown) that receives ultrasound signals measured by the distributed set of sensors and converts the ultrasound signal into a digital signa. Accordingly, the echo processing module 330 may encode the received ultrasound signal(s) into a feature vector, or any other format suitable to be processed by the sensor distance model. To predict the distance between the detector and the transmitter, the model may be a mathematical function or other more complex logical structure, trained using a combination of historical ultrasound signal data collected for the joint to determine a set of parameter values stored in advance and used as part of the predictive analysis. As described herein, the term "model" refers to the result of the machine learning training process. Specifically, the sensor distance model describes the function for predicting the distance between a transmitter and a detector and the determined parameter values for the function. "Parameter values" describe the weight associated with at least one of the featured principal components.

The sensor distance model implemented by the echo processing module 330 is trained using a training dataset made up of a large volume of historical ultrasound signal data collected from detectors and transmitters positioned at various distances around different joints with varying bone structures and bone properties. Accordingly, the sensor distance model is trained to predict the distance between a transmitter and a detector based on physiological properties of the joint (e.g., bone structure and density) and properties of the received ultrasound signal. In some embodiments, the sensor distance model may be trained to generate predictions for a particular joint, for example a knee, or a particular type of joint. In such embodiments, the training dataset upon which the model is trained comprises historical ultrasound signal data collected for a population of users wearing a knee wrap.

Each entry of the training dataset represents a record of distance measurements determined between two sensors labeled with properties of the signal itself and properties of the joint at which the signal was applied. During training, the sensor distance model determines parameter values for each encoded feature (e.g., property of the ultrasound signal and joint) of the feature vector input to the model by analyzing and recognizing patterns and correlations between the collected signal and joint properties and the labeled distance between the transmitter and detector. As patterns and correlations are confirmed by providers, new signals data is collected for existing users continuing to use the wearable ultrasound system 110, and sensor data is collected for new users beginning to use the system 110. The training dataset on which the model is trained may be continuously updated with entries pertaining to the new sensor data. Accordingly, the echo processing module 330 may iteratively train the sensor distance model based on the updated data in the training dataset to continuously improve performance of the sensor distance model. Techniques for training a machine-learned model, for example the sensor distance model, are further discussed below with regards to their implementation by the bone displacement module 340.

The bone displacement module 340 implements a machine-learned model—a displacement model—trained to generate a model or virtual representation of the space surrounding the joint by determining bone displacement at the joint based on the detection of the drive signal and echoes of the drive signal by detectors of the distributed set of sensors. The bone displacement module 340 may encode the received ultrasound signal(s) into a feature vector, or any other format suitable to be processed by the sensor distance model. In one embodiment, the feature vector is a matrix where each value of the matrix is a numerical representation of a feature value extracted from an ultrasound signal.

The displacement model may be a mathematical function or other more complex logical structure, training using a combination of historical ultrasound signals, measurements of distances between sensors responsible for the historical ultrasound signals and known bone displacement measurements corresponding to each historical ultrasound signal. By analyzing the received ultrasound signals and echoes, the distance from between each sensor may be determined and the displacement model may be determine bone displacement measurement based on the delayed or delayed multi-path signals.

To predict the distance between the detector and the transmitter, the model may be a mathematical function or other more complex logical structure, trained using a combination of historical ultrasound signal data collected for the joint to determine a set of parameter values stored in advance and used as part of the predictive analysis. Specifically, the bone displacement module 340 describes the function for predicting the displacement or movement of bones at a particular joint and the determined parameter values incorporated into the function. Examples of the bone displacement model include, but are not limited to, a neural network, a regression model, or any other kernel transformation technique suitable for mapping the inputs to model to bone displacements. Before inputting an encoded representation of the measured ultrasound signals to the bone displacement model, an operator may tune the model for a particular output mapping, for example displacement from tibia to fibula. In alternate embodiments, the bone displacement module 340 may store multiple models, each trained for a particular output mapping (e.g., displacement between two particular bones or displacement at a particular joint).

The bone displacement module 340 trains the bone displacement model using a training dataset made up of a large volume of historical ultrasound signals collected for a population of users, the distance between the transmitter and detector for each ultrasound signal, and the known bone displacement measured for each historical ultrasound signal. In some embodiments, the bone displacement model may be trained to generate predictions for a particular joint, for example a knee. In such embodiments, the training dataset upon which the model is trained comprises historical ultrasound signal data collected for a population of users wearing a knee wrap.

Each entry of the training dataset represents a record of ultrasound signals labeled with an identifier of the joint for which each historical signal was measured, the distance between the transmitter and detector measuring the historical signal, and the bone displacement measured based on the historical signal. During training, the bone displacement model determines parameter values for each encoded feature (e.g., ultrasound signal collected by the ultrasound array) of the feature vector input to the model by analyzing and recognizing patterns and correlations between the collected ultrasound signals and the labeled displacement or positions of bones at the joint. As patterns and correlations are confirmed by providers, new sensor data is collected for existing users continuing to wear a plyowrap, and sensor data is collected for new users beginning to wear a plyowrap, the training dataset on which the model is trained may be continuously updated with entries pertaining to the new sensor data. Accordingly, the bone displacement model may be iteratively trained based on the updated data in the training dataset to continuously improve the accuracy of displacement measurements generated by the bone displacement module 340. In some embodiments, the training dataset used to train the bone displacement model may include data comprising the dataset used to train the sensor distance model updated with labels of known bone displacement measurements for each historical ultrasound signal.

During training, the bone displacement module 340 inputs feature vector representations of the historical ultrasound signals, measured physiological properties of the joint, and measured distances between sensors corresponding to each historical ultrasound signal to the bone displacement model, which outputs a prediction regarding the bone displacement of the joint at the time when the historical ultrasound signals were measured. The bone displacement module 340 compares bone displacement prediction to the actual, known bone displacement measured (e.g., the "ground truth" for the training data) and determines whether the model's prediction was within a threshold tolerance of the ground truth (e.g., a threshold level of accuracy). As described herein, ground truth bone displacement measurements may be collected from different sources including, but not limited to, models of joint and soft tissue previously created and imaged using the wearable ultrasound system 100, measurements taken for patients and cadavers using imaging techniques, and synthetic data generated by applying simulated ultrasound signals to mathematical (virtual) models representing a joint to provide accurate measurements of bone displacement and ultrasound signal propagation.

The bone displacement model is iteratively trained based on new and update training data until it generates bone displacement predictions that satisfy the threshold tolerance of the ground truth. In some embodiments where the bone displacement model does not satisfy the threshold tolerance, additional ultrasound sensors may be added to the distributed set of sensors in areas between existing sensors of the distributed set to collect additional ultrasound signals. The iterative training process described above may be repeated for a variety of joints, where each joint is flexed to different positions of interest.

The echo processing module 330 may also apply the machine-learning techniques described herein with reference to the bone displacement model to train and implement the sensor distance model discussed above.

The bone property module 350 measures physiological properties of the bone or tissue surrounding a joint based on features extracted from ultrasound signals emitted and received by the transmitters and detectors of the distributed set of ultrasound sensors. Examples of physiological properties of the tissue include, but are not limited to, density, strength, and vascularity. Examples of physiological properties of the bones at the joint include, but are not limited to, elasticity, strength, and vascularity.

The bone property module 350 may estimate the quality and or density of bones at a joint because bone density affects the speed of sound propagation. Accordingly, the bone property module 350 estimates bone density based on the delay in signal received by detectors and the quality of each received signal or echo. The bone property module 350 combines delayed echoes of drive signals measured by the echo processing module 330, for example using a frequency domain-based correlator. When performing frequency domain signal processing, the bone property module 350 recognizes cross-correlation between signals as a measure of similarity of two series, determined based on the displacement of one relative to the other. In one embodiment, the bone property module 350 may apply Fourier domain cross correlation or use machine-learning based mapping to assess which waveform delays arise due to certain physiological features. As discussed above, the echo processing module 330 and/or the bone analysis module 320 measures the timing of the drive signals emitted by a transmitter and received by detectors, whether the drive signal be a pulse in the sequential implementation or an orthogonal encoding in the parallel implementation.

As discussed above, where the drive signal reflects between two bones, each reflection off either bone generates a copy of the drive signal. One or more detectors of the distributed set of ultrasound sensors receive the copy of the signal. The bone property module 350 characterizes the distance between two bones based on the time delay between each copy of the drive signal received by the detector. In some embodiments, the bone property module 350 identifies which bones are being measured by identifying the different surface interactions of certain bone pairings, for example patella to tibia or tibia to fibula.

For pulses that traverse through bones (e.g., the tibia or fibula), the bone property module 350 may determine or characterize bone density based on the total time for the drive signal to travel along the direct path and the amount of time for the detector(s) to receive echoes of the drive signal. For example, sound travels faster through a healthy bone, so the time for a detector an opposite side of the joint to receive an echo is directly proportional to the bone density measurement. Accordingly, the bone property module 350 may measure (or predict) bone density based on a measured time delay of echoes for a particular drive signal and known anatomic measurements of the speed of sound through bones of varying density. In some embodiments, the bone property module 350 applies machine correlations of echo-drive signal relationships measured for healthy users and users who have previously measured bone density deficiencies. By correlating the timings measured for each echo-drive signal relationship with the measured bone density and quality, the bone property module 350 may numerically estimate bone characteristics at the joint. In other embodiments, the bone property module 350 may implement a multi-lag cross correlator matrix using the techniques discussed above regarding the bone displacement model of the bone displacement module 340.

Figure 4:
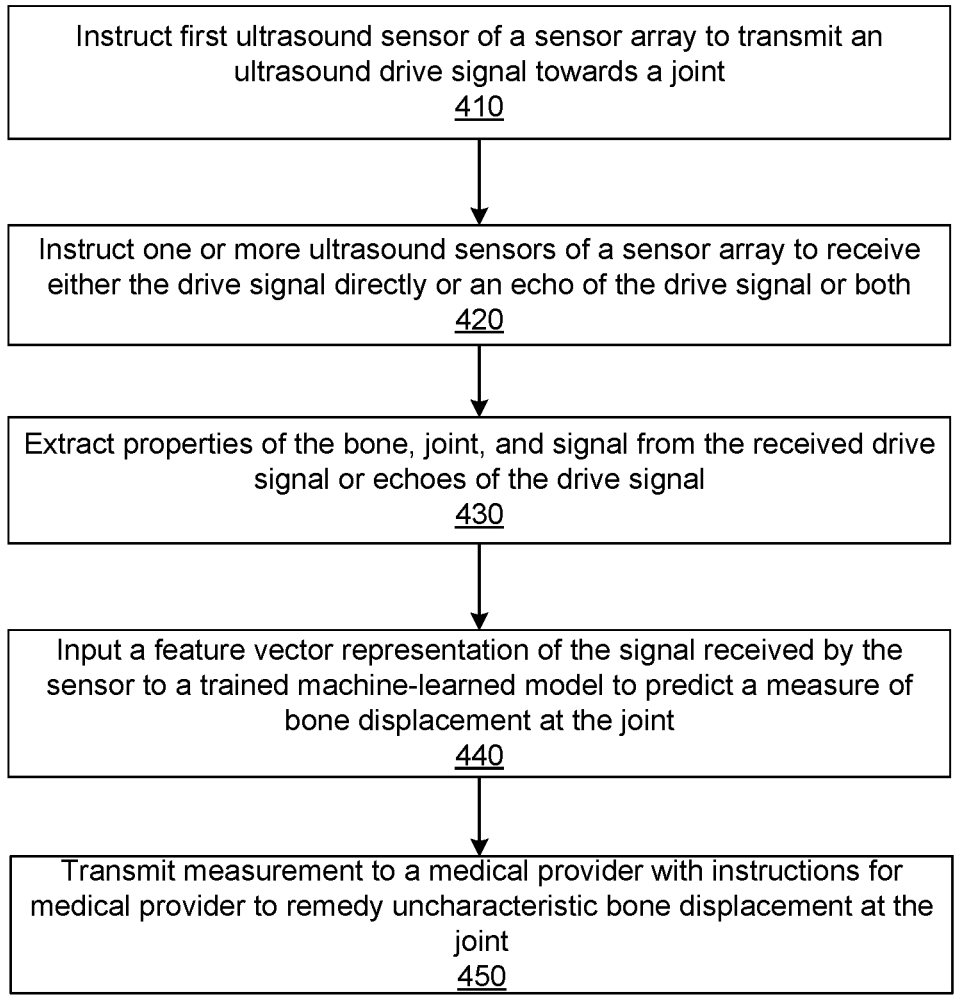
FIG. 4 is an exemplary data flow for predicting bone displacement at a joint using a distributed set of ultrasound sensors, according to an embodiment.

FIG. 4 is an exemplary data flow for predicting bone displacement at a joint using a distributed set of ultrasound sensors, according to an embodiment. The wearable imaging system 110 instructs 410 a first ultrasound sensor of a distributed set of sensors transmit an ultrasound drive signal towards a joint. Additionally, the wearable imaging system 110 instructs 420 one or more ultrasound sensors of a distributed set of sensors to operate in a mode that detects the drive signal directly or an echo of the drive signal indirectly. In some embodiments, the detecting sensor detects both direct signals and indirect echoes of the drive signal. When operating in the sequential implementation described above, the wearable imaging system 110 instructs a single ultrasound sensor to transmit a drive signal and instructs all remaining sensors to detect the drive signal or echoes of the drive signal and iterates sequentially until each ultrasound sensor has transmitted a drive signal. When operating in the parallel implementation, the wearable imaging system 110 instructs all ultrasound sensors to transmit a drive signal encoded with a unique identifier of the transmitting sensor at the same time and immediately instructs all sensors to transition to a mode that detects both direct signals and indirect echoes of all transmitted drive signals.

The wearable imaging system extracts 430 properties of the drive signal and echoes of the drive signal detected by the receiving sensors. Based on the properties of the drive signal and known properties bones and tissue surrounding the joint, the wearable imaging predicts bone-to-bone displacement at the joint. As discussed above with reference to FIG. 3, the wearable imaging system trains a machine-learned model, for example a neural network, to predict bone displacement based on various inputs including bone properties, tissue properties, properties of the ultrasound sensors, properties of the signals transmitted by the ultrasound sensors, or a combination thereof. Accordingly, the wearable imaging system extracts such properties from the detected signals and encodes these properties into a feature vector or representation and inputs 440 the feature vector representation of the signal to the trained model to predict a measure of bone displacement at the joint.

In some embodiments, the wearable imaging system 110 may determine that the predicted bone displacement deviates from a threshold displacement (or an acceptable level of displacement measured for a properly performing or functioning joint). In such embodiments, the wearable imaging system 110 may transmit the measurement to a medical provider and may offer a recommendation for remedying the bone displacement the joint.

Figure 5A:
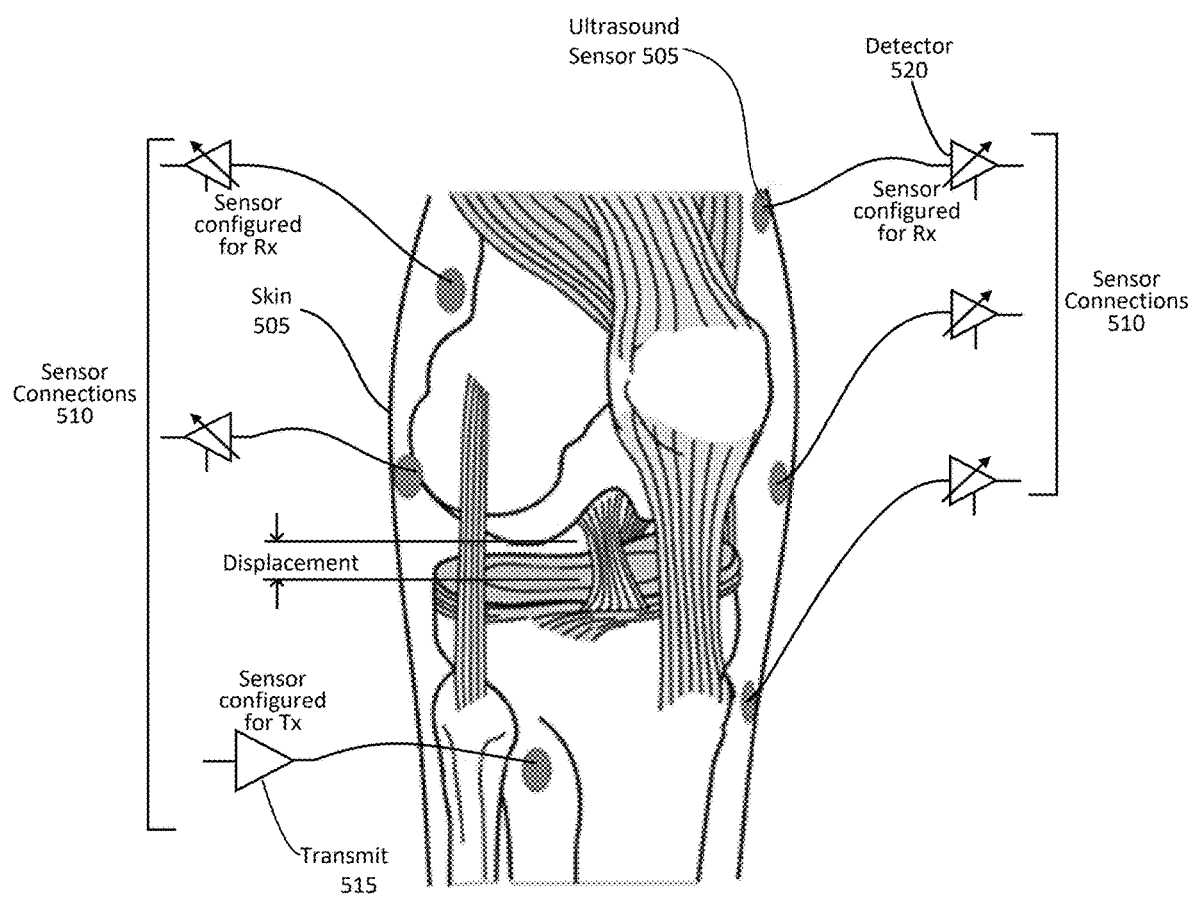
FIGS. 5A-5G illustrate example implementations of the distributed set of sensors and the ultrasound signal processing techniques implemented by the wearable imaging system, according to an embodiment.
Figure 5B:
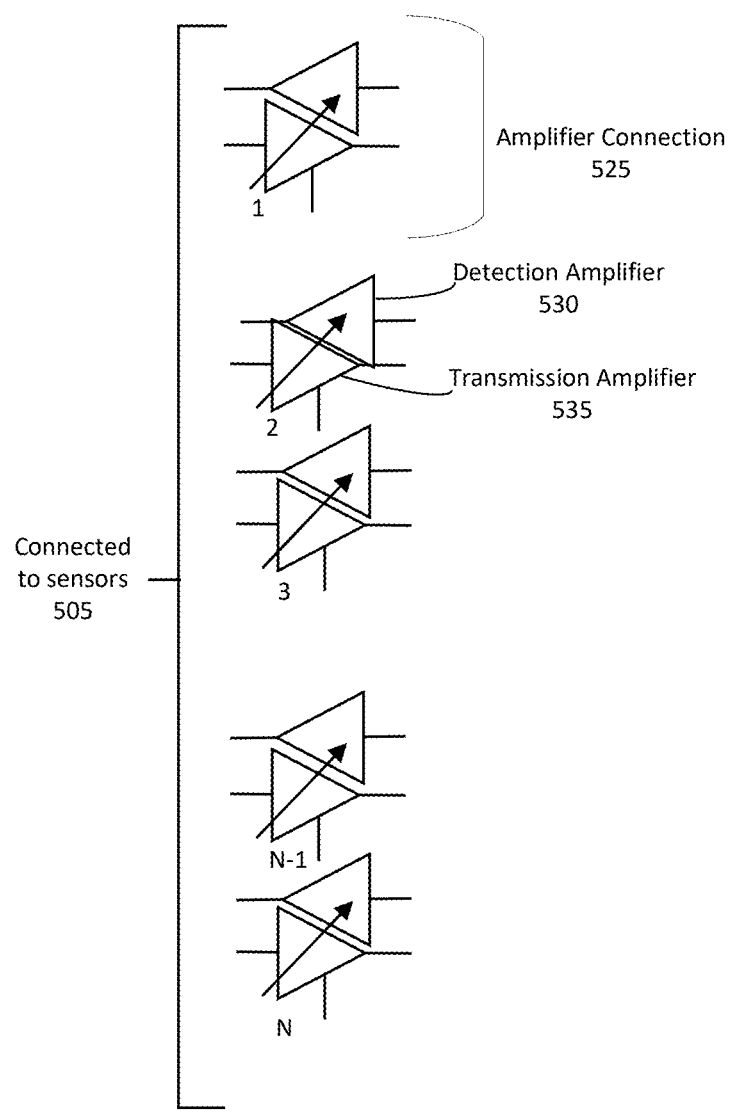

FIGS. 5A-5G illustrate example implementations of the distributed set of sensors and the ultrasound signal processing techniques implemented by the wearable imaging system, according to an embodiment. FIG. 5A illustrates a distributed set of ultrasound sensors 505. In the illustrated embodiment, the distributed set includes five sensors placed directly on the skin of a user surrounding the joint. Each ultrasound sensor 505 is connected to a gain controllable switchable amplifier, hereafter referred to as a sensor connection 610. FIG. 5A illustrates a distributed set of sensors operating in a sequential implementation, according to an embodiment. A single sensor (e.g., transmitter 515) operates in transmission mode to emit an ultrasound signal and the remaining sensors, including the detector 620, operate in detection mode to receive the emitted ultrasound signal. A controller of the wearable imaging system, for example the controller 170, transmits digital signal to switch each sensor between the transmission mode and the detection mode via the switchable amplifier of the sensor connection 610. FIG. 5B illustrates amplifier connections for sensor connections 610 for a distributed set n ultrasound sensors, according to an embodiment. Each sensor amplifier 525 comprises a detection amplifier 530 and a transmission amplifier 535, which the controller 170 selectively activates or deactivates depending on the implementation, cycle of the implementation, or role of the connected sensor during that cycle.

Figure 5C:
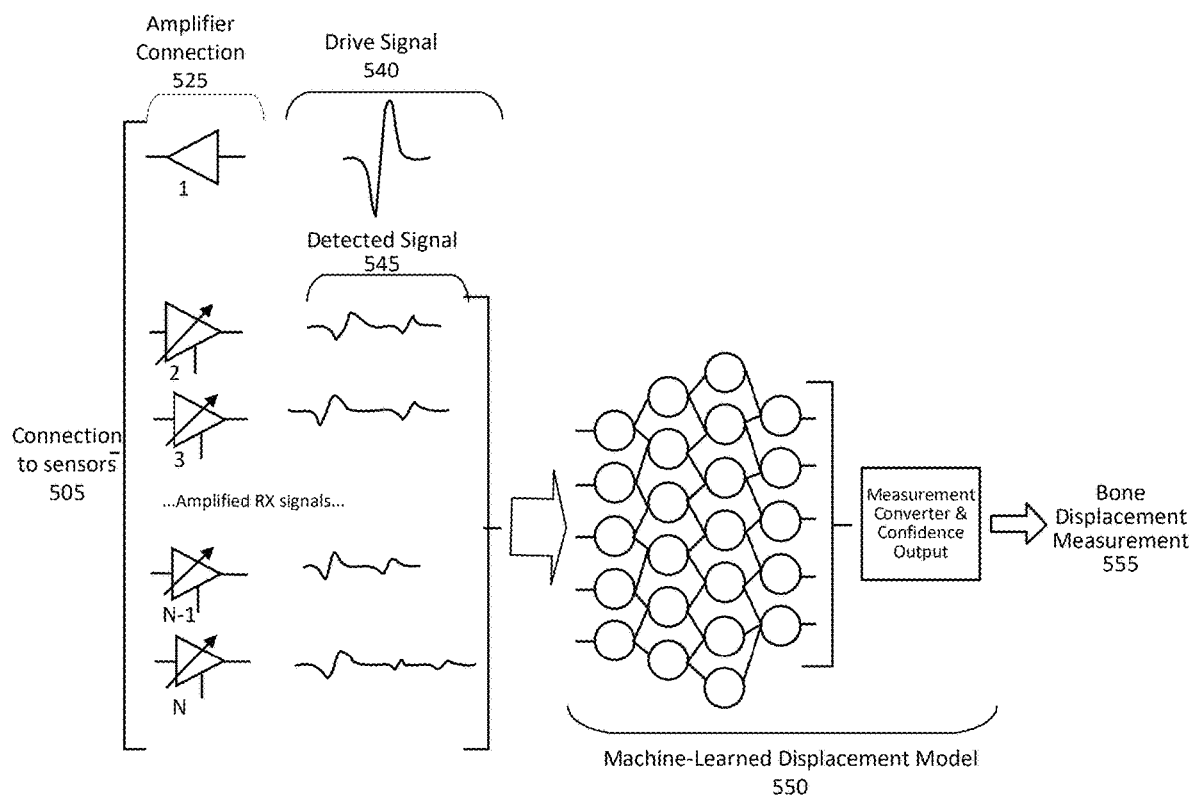
Figure 5D:
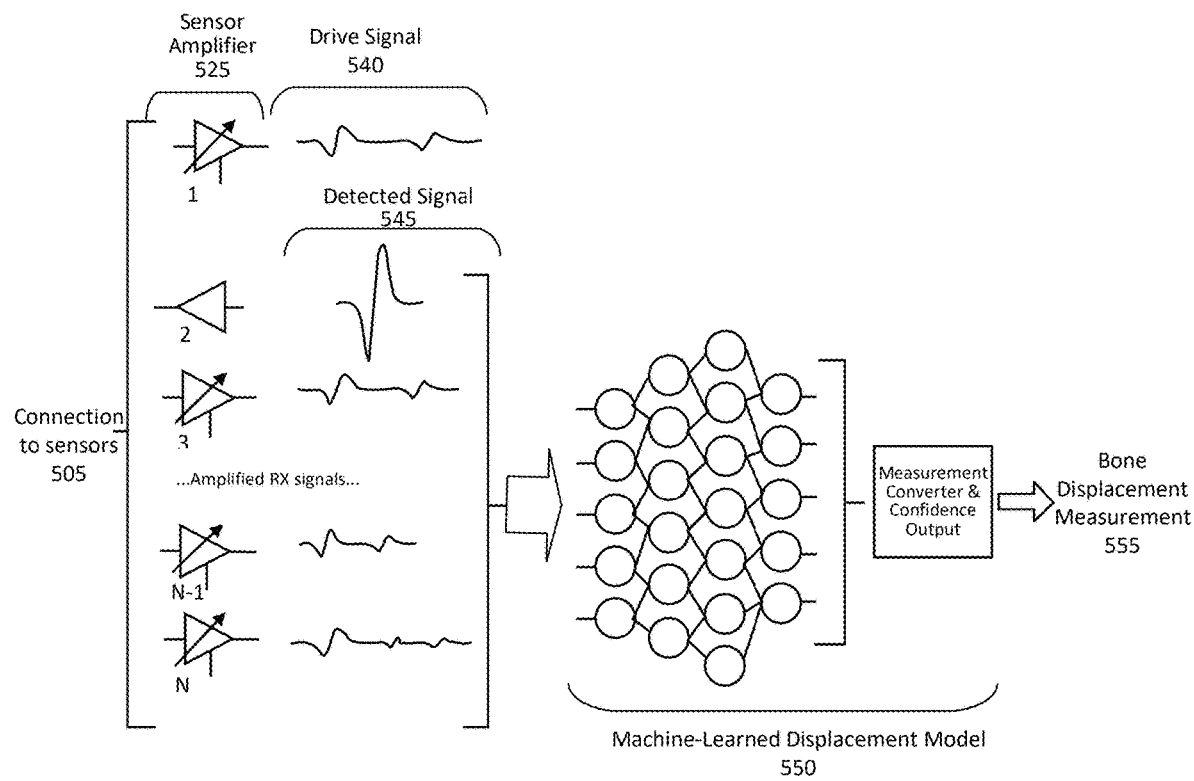

FIG. 5C illustrates a distributed set of sensors operating in a sequential implementation, according to an embodiment. The first sensor, operating in transmission mode to emit a drive signal 540, while the remaining sensors (e.g., sensors 2 through "n") operating in detection mode to detect the signal 545 at different times and with different reflections. Accordingly, the transmitting sensor (e.g., the transmitter) emits the drive signal 540 as a formed shape, while the detecting sensors (e.g., the detectors) detect the signal 545 at different times and different reflections. The variance in time of detection and reflections causes the shape of the input signals 540 for the detectors to vary. The machine-learned displacement model 550 (consistent with the description above) is trained to distinguish direct transmissions of the signal (e.g., signals transmitted directly from the transmitter to a detector) from echoes of the signal (e.g., signals affected due to reflections and resonance). By analyzing all detected ultrasound signals, the controller 170 may determine the distance from each sensor to the others and determine the bone displacement based on secondary patterns derived from the detected ultrasound signals, for example delays or multi-path delays. The output of the machine-learned displacement model 550 is a bone displacement measurement 555. Accordingly, consistent with the description above, the machine-learned displacement model 550 is trained using a training dataset of measured data to model the relationship between ultrasound interactions and bone displacement. In some embodiments, the displacement model 550 determines a confidence interval for an output when determining whether to accept the output. In FIG. 5D, the controller switches the amplifier connection of the first sensor to operate in detection mode and switches the amplifier connection of the second sensor to operate in transmission mode. Accordingly, the second sensor now emits the drive signal as an output and the first signal receives (or detects) the drive signal as an input. The controller 170 repeats this process of switching operation of each sensor's amplifier until all sensors 505 have transmitted an ultrasound signal in transmission mode.

Figure 5E:
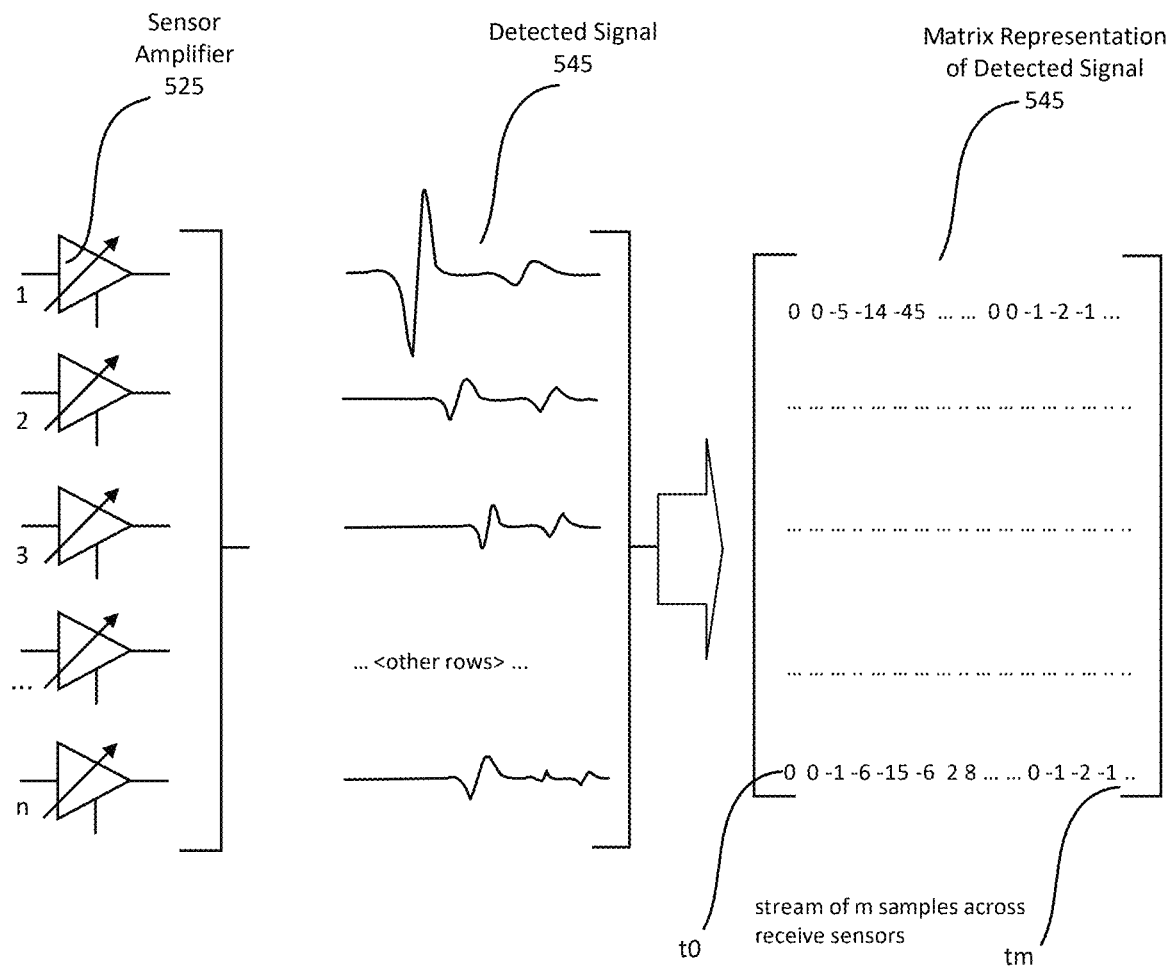

FIG. 5E illustrates the conversion of detected ultrasound signals into a representation capable of being processed by the machine-learned bone displacement model 550, according to an embodiment. In the illustrated diagram, each sensor amplifier 525 is switched into detection mode such that each sensor detects a signal 545, either a direct transmission of the drive signal or an echo of the drive signal. The controller 170 converts each detected signal 545 into a timeseries (or matrix) representation 545 which may be input the to the machine-learned displacement model 550. Each row of the matrix represents a detected signal received a particular detector, such that the generated matrix represents a stream of m samples across the detectors of the distributed set of sensors.

Figure 5F:
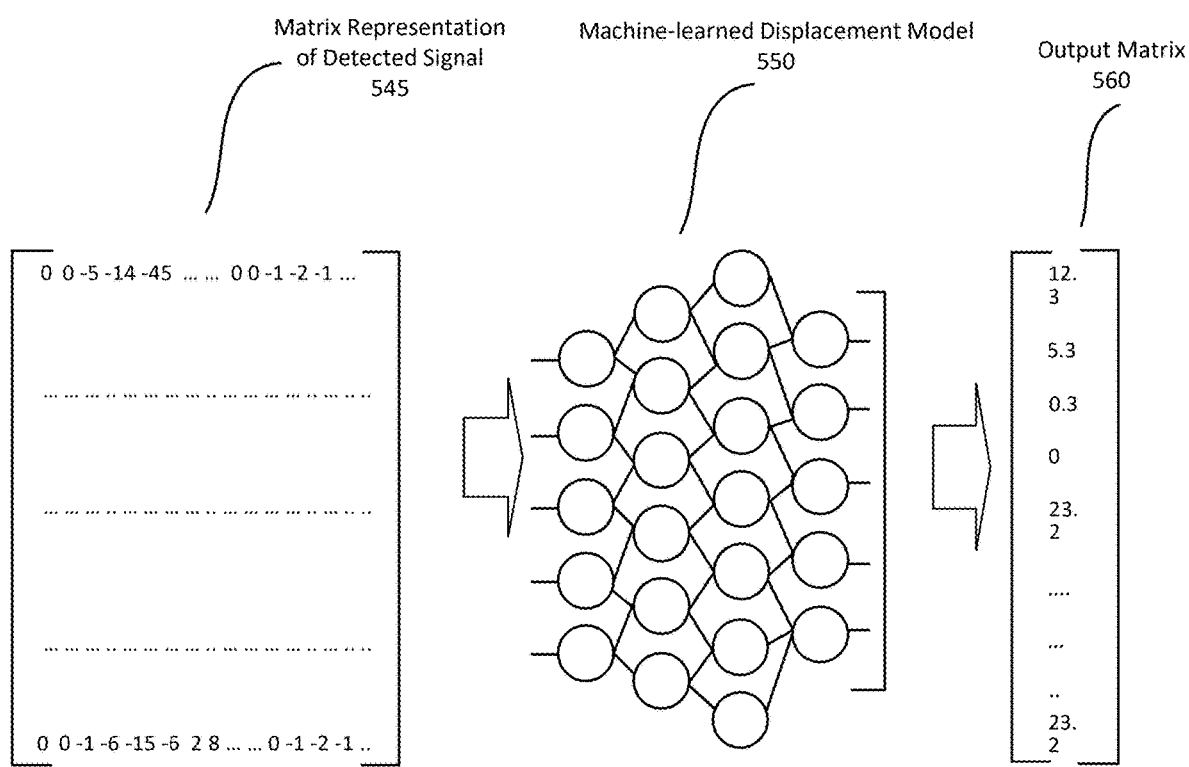
Figure 5G:
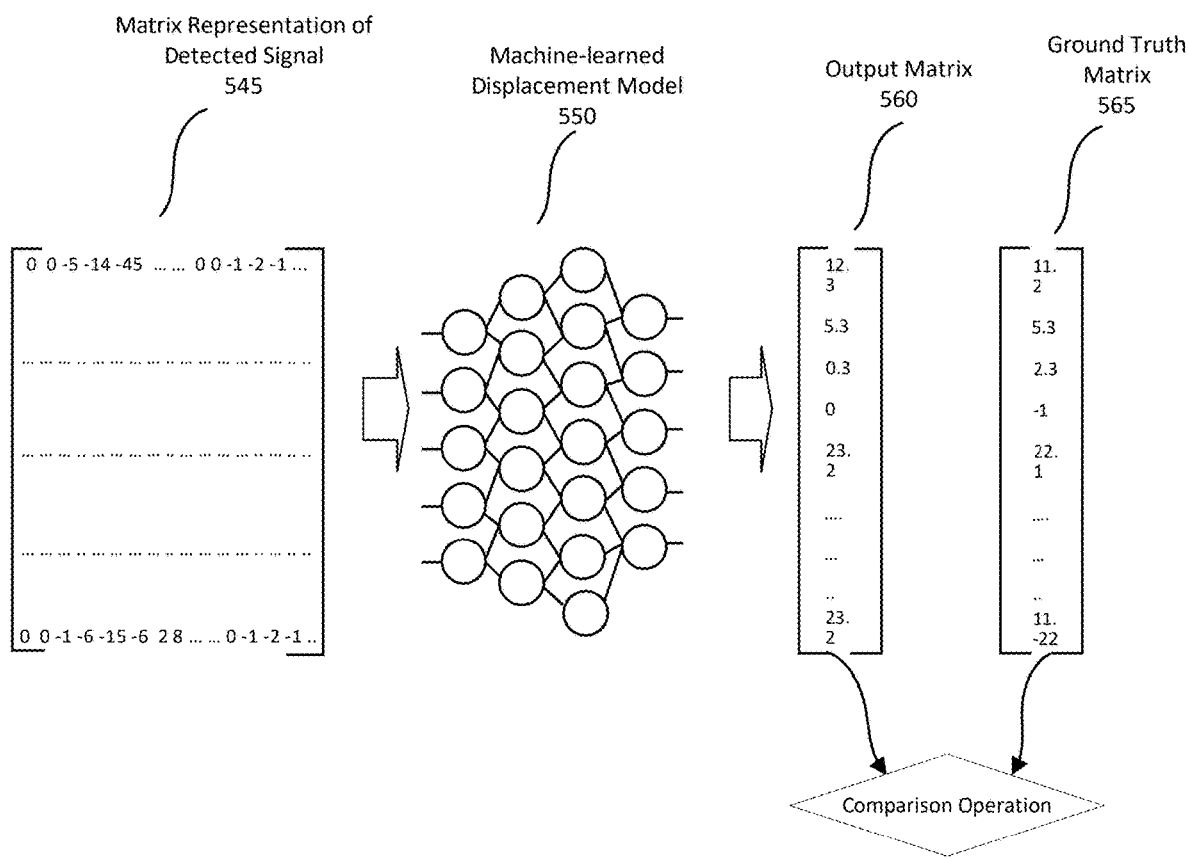

FIG. 5F illustrates generation a bone displacement measurement from a matrix representation of the detected signals, according to an embodiment. The encoded matrix representation 545 is input to the machine-learned displacement model 550 to output a matrix transformation, for example the output matrix 560. The displacement model 550 may be feed forward neural network, or any other suitable kernel transformation trained to map an input matrix to bone displacement measurements. Although the initial mapping by the model 550 may be inaccurate, the controller 170 may improve the accuracy of the model by iteratively training the model. FIG. 5G illustrates the iterative training of the model 550 based on inaccurate predictions by the model 550, according to an embodiment. In FIG. 5G, the output of the initial feed forward pass produced an output 560 which can be compared against a matrix of ground truth measurements 565. Through an interactive process, the controller 170 receive the output 560 and train the model 550 to create an output that provides measurements within an acceptable accuracy. Where measurements of the output matrix 550 are not within a threshold deviation of the ground truth measurement, the controller 170 may update the training dataset by placing additional sensors around the joint or by collecting additional signals from already placed sensors.

V. Example Machine Architecture

Figure 6:
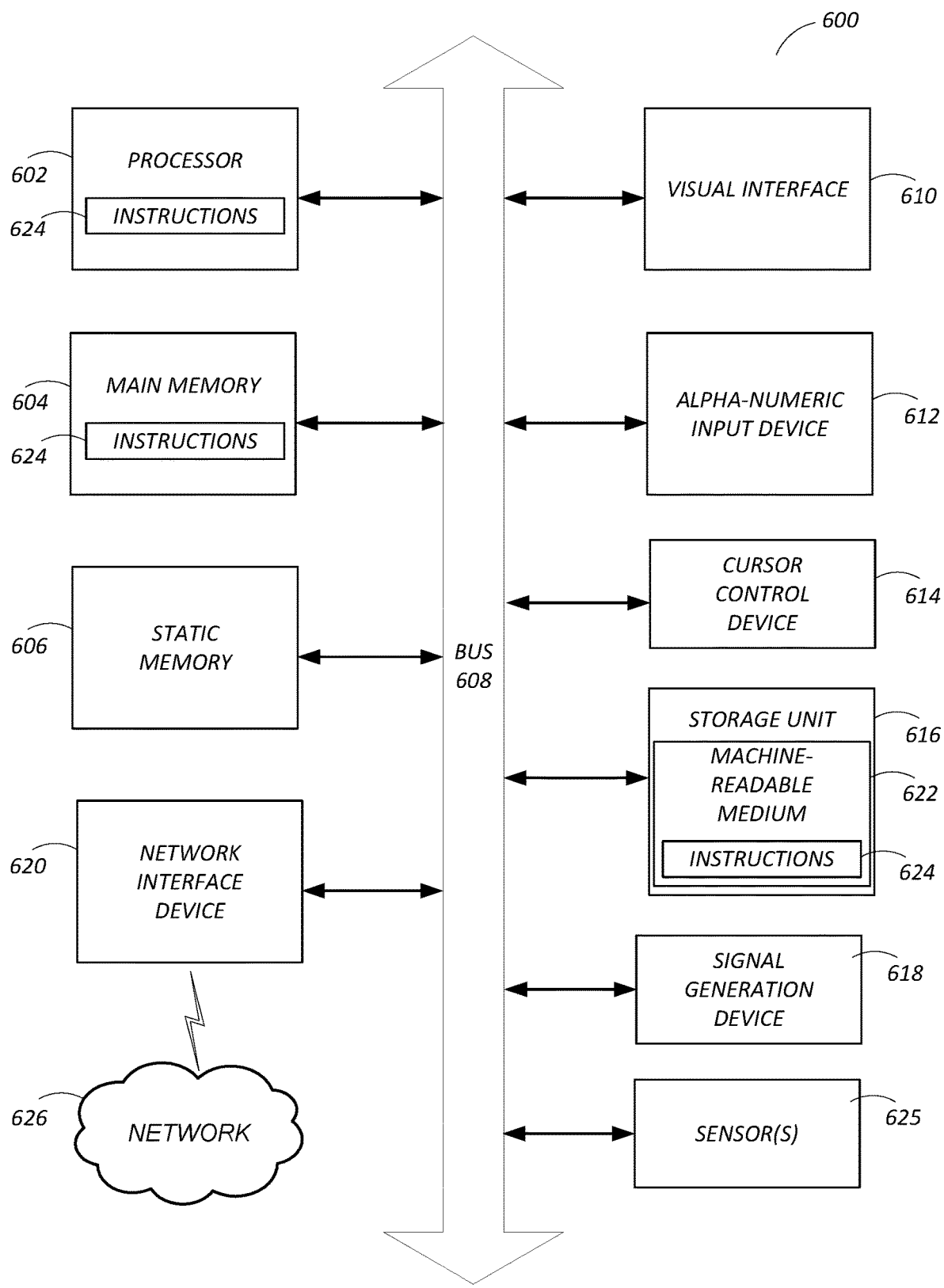
FIG. 6 is a block diagram illustrating components of an example machine able to read instructions from a machine-readable medium and execute them in a processor (or controller), according to one example embodiment.

FIG. 6 is a block diagram illustrating components of an example machine able to read instructions described as processes herein from a machine-readable medium and execute them in at least one processor (or controller). Specifically, FIG. 6 shows a diagrammatic representation of a machine in the example form of a computer system 600. The computer system 600 can be used to execute instructions 624 (e.g., program code or software) for causing the machine to perform any one or more of the methodologies (or processes) described herein. In alternative embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment. It is noted the instructions correspond to the functionality of components and/or processes described herein, for example, with respect to FIGS. 1-5.

The machine may be a server computer, a client computer, a personal computer (PC), a tablet PC, a set-top box (STB), a smartphone, an internet of things (IoT) appliance, a network router, switch or bridge, or any machine capable of executing instructions 624 (sequential or otherwise) that specify actions to be taken by that machine. Further, while only a single machine is illustrated, the term "machine" shall also be taken to include any collection of machines that individually or jointly execute instructions 624 to perform any one or more of the methodologies discussed herein.

The example computer system 600 includes one or more processing units (generally processor 602). The processor 602 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. The computer system 600 also includes a main memory 604. The computer system may include a storage unit 616. The processor 602, memory 604 and the storage unit 616 communicate via a bus 608.

In addition, the computer system 600 can include a static memory 606, a display driver 610 (e.g., to drive a plasma display panel (PDP), a liquid crystal display (LCD), or a projector). The computer system 600 may also include alphanumeric input device 612 (e.g., a keyboard), a cursor control device 614 (e.g., a mouse, a trackball, a joystick, a motion sensor, or other pointing instrument), a signal generation device 618 (e.g., a speaker), and a network interface device 620, which also are configured to communicate via the bus 608.

The storage unit 616 includes a machine-readable medium 622 on which is stored instructions 624 (e.g., software) embodying any one or more of the methodologies or functions described herein. The instructions 624 may also reside, completely or at least partially, within the main memory 604 or within the processor 602 (e.g., within a processor's cache memory) during execution thereof by the computer system 600, the main memory 604 and the processor 602 also constituting machine-readable media. The instructions 624 may be transmitted or received over a network 526 via the network interface device 620.

While machine-readable medium 622 is shown in an example embodiment to be a single medium, the term "machine-readable medium" should be taken to include a single medium or multiple media (e.g., a centralized or distributed database, or associated caches and servers) able to store the instructions 624. The term "machine-readable medium" shall also be taken to include any medium that is capable of storing instructions 624 for execution by the machine and that cause the machine to perform any one or more of the methodologies disclosed herein. The term "machine-readable medium" includes, but not be limited to, data repositories in the form of solid-state memories, optical media, and magnetic media. It is noted that in some example embodiments, the core components of the computer system may disregard components except for the processor 602, memory 604, and bus 608 and may in other embodiments also include the storage unit 616 and/or the network interface device 620.

Also illustrated is sensor(s) 625 which may correspond to the one or more sensors described herein, for example, ultrasound sensors 205, 235 and 255. The sensors 525 collect data that may be stored, e.g., in the storage unit 616 and/or memory 604 and/or 606, and may be used by the instructions 624 for processing by processor 602.

VII. Additional Considerations

The wearable imaging system 100 disclosed herein is associated with numerous benefits and improvements over conventional ultrasound imaging systems. First, the plyowrap of the wearable imaging system 100 is embedded with ultrasound sensors that interface directly with the skin of a user, which eliminates the need for a medical provider or operator to manually handle a transducer. This, in turn, also reduces the number of personnel required to be present in a procedure room during an operation or intervention. Second, the integrated array of ultrasound sensors for measuring bone displacement reduce/limit/eliminate radiation exposure by providing real-time non-radiation-based image feedback to both the user and the operator. Third, the disclosed configuration can reduce procedure time and improve decision making during a procedure for anatomic identification, anatomic alignment, anatomic placement, implant delivery, implant placement, and invasive intervention.

The distributed set of ultrasound sensors facilitates the placement of trocars and the anatomic alignment of bone tunnels, which provides greater precision than conventional arthroscopic visualization to estimate the location of the bone tunnel. The distributed set of ultrasound sensors integrated int the plyowrap has multiple openings for accessing a particular body part, where the customary placement of incisions and portals are made for arthroscopic surgery.

Although described herein in the context of a medical or clinical setting, a person having ordinary skill in the art would recognize and appreciate that the systems and techniques described herein may be applied in any industry that would require a real-time and/or real-world ultrasound, for example activities involving drilling, tapping, exploring, or monitoring.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms, for example, as illustrated and described with FIGS. 1-4. Modules may constitute either software modules (e.g., code embodied on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may include dedicated circuitry or logic that is permanently configured (e.g., as a special-purpose processor, such as a field programmable gate array (FPGA) or an application-specific integrated circuit (ASIC)) to perform certain operations. A hardware module may also include programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors, e.g., processor 602, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, include processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that includes a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the claimed invention. This description should be read to include one or at least one and the singular also includes the plural unless it is obvious that it is meant otherwise.

Upon reading this disclosure, those of skill in the art will appreciate still additional alternative structural and functional designs for a wearable imaging system. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
    transmitting a digital signal to a distributed set of sensors positioned around a joint of a user, the digital signal comprising a first set of instructions for one or more sensors of the distributed set of sensors to emit ultrasound signals towards the joint of the user and a second set of instructions for sensors of the distributed set of sensors to detect ultrasound signals traveling through structures of the joint and echoes of ultrasound signals reflected off structures of the joint;
    extracting physiological properties of bones connected at the joint and tissue surrounding the joint from features of the detected echoes of ultrasound signals, wherein the extracted physiological properties comprise one or more of: elasticity, density, strength, and vascularity;
    generating a bone displacement measurement of the bones connected at the joint, wherein generating the bone displacement measurement comprises:
        inputting the physiological properties of the joint and properties of the detected echoes of ultrasound signals to a machine-learning displacement model trained to generate a virtual representation of a space surrounding the joint, wherein the displacement model is trained using a training dataset of historical ultrasound signals collected from a population of users, each entry of the training dataset comprising historical ultrasound signals detected for a joint and labeled with an identifier of the joint and a known bone displacement measurement at the labeled joint; and
        determining the bone displacement measurement based on a distance between a sensor of the distributed set of sensors emitting ultrasound signals and a sensor of the distributed set of sensors detecting echoes of ultrasound signals, wherein the bone displacement measurement describes a movement of bones connected at the joint; and
    responsive to determining that the bone displacement measurement at the joint exceeds a threshold displacement, transmitting the bone displacement measurement to a medical provider of the user.

2. The method of claim 1, wherein the first set of instructions cause each sensor of the distributed set of sensors to simultaneously emit ultrasound signals and the second set of instructions cause each sensor of the distributed set of sensors to detect ultrasound signals immediately after transmission of an ultrasound signal, wherein the ultrasound signal emitted by each sensor of the distributed set of sensors is encoded with a unique signature identifying the sensor.

3. The method of claim 1, wherein the machine-learning displacement model is iteratively re-trained as the training dataset is updated with new ultrasound signals measured through joints of new users of the distributed set of sensors and existing users continuing to use the distributed set of sensors.

4. The method of claim 1, wherein the machine-learning displacement model is a neural network.

5. The method of claim 1, further comprising:
    for each ultrasound signal detected by sensors of the distributed set of sensors, convert the ultrasound signal into a digital signal; and
    input a representation of the digital signal into a machine-learning distance model to generate a distance measurement between the sensor transmitting the ultrasound signal and the sensor detecting the ultrasound signal, the machine-learning distance model trained using a training dataset of historical ultrasound signals collected from sensors at varying distances apart.

6. The method of claim 1, further comprising:
    determining a time delay between emission of an ultrasound signal by a sensor of the distributed set of sensors and detection of a reflection of the ultrasound signal by at least one other sensor of the distributed set of sensors; and
    determining a density of bones at the joint based on the time delay and measured speed of sound through bones at the joint.

7. The method of claim 1, wherein the first set of instructions cause a first sensor of the distributed set of sensors to emit a first ultrasound signal and the second set of instructions cause the remaining sensors of the distributed set of sensors to detect the first ultrasound signal.

8. The method of claim 7, wherein the first set of instructions cause a second sensor of the distributed set of sensors to emit a second ultrasound signal in response to the detection of the first ultrasound signal by the remaining sensors of the distributed set of sensors.

9. A wearable imaging system comprising:
    a distributed set of sensors secured around a joint of a user, the distributed set of sensors comprising:
        one or more sensors configured to emit ultrasound signals towards the joint of the user; and
        sensors configured to detect ultrasound signals traveling through structures of the joint and echoes of ultrasound signals reflected off structures of the joint; and
    a controller configured to:
        transition each sensor of the distributed set of sensors between a first mode pertaining the one or more sensors emitting ultrasound signals and a second mode pertaining to sensors detecting ultrasound signals traveling through structures of the joint;
        extract physiological properties of bones connected at the joint and tissue surrounding the joint from features of the detected echoes of ultrasound signals, wherein the extracted physiological properties comprise one or more of: elasticity, density, strength, and vascularity;
        generating a bone displacement measurement of the bones connected at the joint, wherein the controller generates the bone displacement measurement by:
            inputting the physiological properties of the joint and properties of the detected echoes of ultrasound signals to a machine-learning displacement model trained to generate a virtual representation of a space surrounding the joint, wherein the displacement model is trained using a training dataset of historical ultrasound signals collected from a population of users, each entry of the training dataset comprising historical ultrasound signals detected for a joint and labeled with an identifier of the joint and a known bone displacement measurement at the labeled joint; and determining the bone displacement measurement based on a distance between a sensor of the distributed set of sensors emitting ultrasound signals and a sensor of the distributed set of sensors detecting echoes of ultrasound signals, wherein the bone displacement measurement describes a movement of bones connected at the joint; and responsive to determining that the bone displacement measurement exceeds a threshold displacement, transmit the bone displacement measurement to a medical provider of the user.

10. The wearable imaging system of claim 9, wherein each sensor of the distributed set of sensors simultaneously emits ultrasound signals and each sensor of the distributed set of sensors detects ultrasound signals immediately after transmission of the ultrasound signal, wherein the ultrasound signal emitted by each sensor of the distributed set of sensors is encoded with a unique signature identifying the sensor.

11. The wearable imaging system of claim 9, wherein the machine-learning displacement model is iteratively re-trained as the training dataset is updated with new ultrasound signals measured through joints of new users of the distributed set of sensors and existing users continuing to use the distributed set of sensors.

12. The wearable imaging system of claim 9, wherein the controller is further configured to:

convert each ultrasound signal detected by sensors of the distributed set of sensors into a digital signal; and input a representation of the digital signal into a machine-learning distance model to generate a distance measurement between the sensor transmitting the ultrasound signal and the sensor detecting the ultrasound signal, the machine-learning distance model trained using a training dataset of historical ultrasound signals collected from sensors at varying distances apart.

13. The wearable imaging system of claim 9, wherein the controller is further configured to:

determine a time delay between emission of an ultrasound signal by a sensor of the distributed set of sensors and detection of a reflection of the ultrasound signal by at least one other sensor of the distributed set of sensors; and determine a density of bones at the joint based on the time delay and measured speed of sound through bones at the joint.

14. The wearable imaging system of claim 9, wherein a first sensor of the distributed set of sensors emits a first ultrasound signal and each remaining sensor of the distributed set of sensors detects the ultrasound signal.

15. The wearable imaging system of claim 14, wherein a second sensor of the distributed set of sensors emits a second ultrasound signal in response to each sensor configured to detect ultrasound signals detects the first ultrasound signal.

16. A non-transitory computer readable storage medium, storing instructions encoded thereon that, when executed by one or more processors, cause the processors to:

transmit a digital signal to a distributed set of sensors positioned around a joint of a user, the digital signal comprising a first set of instructions for one or more sensors of the distributed set of sensors to emit ultrasound signals towards the joint of the user and a second set of instructions for sensors of the distributed set of sensors to detect ultrasound signals traveling through structures of the joint and echoes of ultrasound signals reflected off structures of the joint;

extract physiological properties of bones connected at the joint and tissue surrounding the joint from features of the detected echoes of ultrasound signals, wherein the extracted physiological properties comprise one or more of: elasticity, density, strength, and vascularity;

generate a bone displacement measurement of the bones connected at the joint, wherein instructions for generating the bone displacement measurement cause the processor to:

input the physiological properties of the joint and properties of the detected echoes of ultrasound signals to a machine-learning displacement model trained to generate a virtual representation of a space surrounding the joint, wherein the displacement model is trained using a training dataset of historical ultrasound signals collected from a population of users, each entry of the training dataset comprising historical ultrasound signals detected for a joint and labeled with an identifier of the joint and a known bone displacement measurement at the labeled joint; and determine the bone displacement measurement based on a distance between a sensor of the distributed set of sensors emitting ultrasound signals and a sensor of the distributed set of sensors detecting echoes of ultrasound signals, wherein the bone displacement measurement describes a movement of bones connected at the joint; and responsive to determining that the bone displacement measurement at the joint exceeds a threshold displacement, transmit the bone displacement measurement to a medical provider of the user.

17. The non-transitory computer readable medium of claim 16, wherein the first set of instructions cause each sensor of the distributed set of sensors to simultaneously emit ultrasound signals and the second set of instructions cause each sensor of the distributed set of sensors to detect ultrasound signals immediately after transmission of an ultrasound signal, wherein the ultrasound signal emitted by each sensor of the distributed set of sensors is encoded with a unique signature identifying the sensor.

18. The non-transitory computer readable medium of claim 16, wherein the machine-learning displacement model is iteratively re-trained as the training dataset is updated with new ultrasound signals measured through joints of new users of the distributed set of sensors and existing users continuing to use the distributed set of sensors.

19. The non-transitory computer readable medium of claim 16, wherein the instructions further cause the processor to:

determine a time delay between emission of an ultrasound signal by a sensor of the distributed set of sensors and detection of a reflection of the ultrasound signal by at least one other sensor of the distributed set of sensors; and determine a density of bones at the joint based on the time delay and measured speed of sound through bones at the joint.

20. The non-transitory computer readable storage medium of claim 16, wherein the first set of instructions cause a first sensor of the distributed set of sensors to emit a first ultrasound signal and the second set of instructions cause the remaining sensors of the distributed set of sensors to detect the first ultrasound signal.

21. The non-transitory computer readable storage medium of claim 20, wherein the first set of instructions cause a second sensor of the distributed set of sensors to emit a second ultrasound signal in response to the detection of the first ultrasound signal by the remaining sensors of the distributed set of sensors.

* * * * *